United States Patent
Yang et al.

(10) Patent No.: US 8,974,375 B2
(45) Date of Patent: Mar. 10, 2015

(54) JOINT ARRANGEMENT

(75) Inventors: Guang-Zhong Yang, London (GB); David Paul Noonan, London (GB); Jianzhong Shang, London (GB); Valentina Vitiello, London (GB)

(73) Assignee: Imperial Innovations Ltd., London (GB)

( * ) Notice: Subject to any disclaimer, the term of this patent is extended or adjusted under 35 U.S.C. 154(b) by 317 days.

(21) Appl. No.: 13/380,005

(22) PCT Filed: Jun. 24, 2010

(86) PCT No.: PCT/GB2010/001237
§ 371 (c)(1),
(2), (4) Date: May 16, 2012

(87) PCT Pub. No.: WO2010/149969
PCT Pub. Date: Dec. 29, 2010

(65) Prior Publication Data
US 2012/0220830 A1    Aug. 30, 2012

(30) Foreign Application Priority Data
Jun. 24, 2009  (GB) .................................. 0910951.3

(51) Int. Cl.
*A61B 1/00* (2006.01)
*A61B 1/008* (2006.01)
*A61B 1/005* (2006.01)

(52) U.S. Cl.
CPC ............... *A61B 1/008* (2013.01); *A61B 1/0053* (2013.01)
USPC ............................ 600/142; 600/141; 600/137

(58) Field of Classification Search
CPC ..... A61B 1/0055; A61B 1/0056; A61B 1/008
USPC ................................................ 600/141, 142
See application file for complete search history.

(56) References Cited

U.S. PATENT DOCUMENTS 3,773,039 A * 11/1973 Mori et al. .................... 600/173
3,942,826 A *  3/1976 Lester ...................... 285/148.27

(Continued)

FOREIGN PATENT DOCUMENTS

JP    2007-029289 A    2/2007
WO    WO 03/028547      4/2003

(Continued)

OTHER PUBLICATIONS

Japan Patent Office, "Notification of Reasons for Refusal", in application No. 2012-516849, dated Nov. 12, 2013, 2 pages.

(Continued)

*Primary Examiner* — Anhtuan T Nguyen
*Assistant Examiner* — Jae Woo
(74) *Attorney, Agent, or Firm* — Hickman Palermo Truong Becker Bingham Wong LLP

(57) ABSTRACT

An actuatable joint is disclosed having a transmission member, for example a ring gear, associated with a member of a joint and rotatable about a longitudinal axis through the member. In particular a two degree of freedom actuatable joint is disclosed comprising tendon driven joint arrangements having a transmission member disposed around or inside a body of the joint arrangement, to provide transmission of a force from a driving means to two tendons actuating a rotational degree of freedom of the joint arrangement. Further disclosed is a segmented device, for example an endoscope, comprising a plurality of such joints, for example to define a flexible and steerable conduit for an instrument.

14 Claims, 46 Drawing Sheets

(56) References Cited

U.S. PATENT DOCUMENTS

| | | | | |
|---|---|---|---|---|
| 4,277,168 | A | * | 7/1981 | Oku ............................ 356/138 |
| 4,503,842 | A | * | 3/1985 | Takayama .................... 600/152 |
| RE34,110 | E | * | 10/1992 | Opie et al. ................... 600/128 |
| 5,337,732 | A | | 8/1994 | Grundfest et al. |
| 5,386,741 | A | | 2/1995 | Rennex |
| 5,402,801 | A | | 4/1995 | Taylor |
| 5,567,110 | A | | 10/1996 | Sutherland |
| 5,662,587 | A | | 9/1997 | Grundfest et al. |
| 5,840,013 | A | * | 11/1998 | Lee et al. ..................... 600/114 |
| 5,906,591 | A | | 5/1999 | Dario et al. |
| 6,610,007 | B2 | * | 8/2003 | Tartaglia et al. .............. 600/146 |
| 6,875,170 | B2 | | 4/2005 | Francois et al. |
| 7,090,637 | B2 | * | 8/2006 | Danitz et al. ................. 600/141 |
| 7,090,683 | B2 | | 8/2006 | Brock et al. |
| 7,154,362 | B2 | | 12/2006 | Ohnstein et al. |
| 7,235,046 | B2 | * | 6/2007 | Anhalt et al. ................. 600/142 |
| 7,316,681 | B2 | | 1/2008 | Madhani et al. |
| 7,369,672 | B2 | * | 5/2008 | Hirschhorn ................... 381/333 |
| 7,615,042 | B2 | * | 11/2009 | Beyar et al. .................. 604/510 |
| 7,789,826 | B2 | * | 9/2010 | Sullivan et al. ............... 600/149 |
| 8,523,766 | B2 | * | 9/2013 | Kudoh et al. ................. 600/146 |
| 2002/0087048 | A1 | | 7/2002 | Brock et al. |
| 2003/0149338 | A1 | | 8/2003 | Francois et al. |
| 2004/0019254 | A1 | * | 1/2004 | Belson et al. ................. 600/146 |
| 2005/0059960 | A1 | | 3/2005 | Simaan et al. |
| 2005/0075538 | A1 | * | 4/2005 | Banik et al. .................. 600/141 |
| 2005/0085693 | A1 | | 4/2005 | Belson et al. |
| 2005/0099254 | A1 | | 5/2005 | Ohnstein et al. |
| 2005/0228224 | A1 | * | 10/2005 | Okada et al. .................. 600/104 |
| 2006/0030841 | A1 | | 2/2006 | Madhani et al. |
| 2006/0178556 | A1 | | 8/2006 | Hasser et al. |
| 2006/0199999 | A1 | | 9/2006 | Ikeda et al. |
| 2006/0287576 | A1 | * | 12/2006 | Tsuji et al. .................... 600/132 |
| 2007/0135803 | A1 | * | 6/2007 | Belson ............................. 606/1 |
| 2008/0045794 | A1 | | 2/2008 | Belson |
| 2008/0064920 | A1 | * | 3/2008 | Bakos et al. .................. 600/102 |
| 2008/0287963 | A1 | | 11/2008 | Rogers et al. |
| 2009/0138025 | A1 | * | 5/2009 | Stahler et al. ................. 606/130 |
| 2010/0004509 | A1 | * | 1/2010 | Naito et al. ................... 600/141 |
| 2013/0035552 | A1 | * | 2/2013 | Moriyama .................... 600/149 |

FOREIGN PATENT DOCUMENTS

| | | |
|---|---|---|
| WO | WO 2005/018428 A2 | 3/2005 |
| WO | WO 2006/094242 A1 | 9/2006 |
| WO | WO 2007/033379 | 3/2007 |

OTHER PUBLICATIONS

Degani et al., "Highly Articulated Robotic Probe for Minimally Invasive Surgery", Proceeding of the 2006 IEEE International Conference on Robotics Automation, dated May 2006, 6 pages.

Szewczyk et al., "An Active Tubular Polyarticulated Micro-System for Flexible Endoscope", dated 2001, 1 page.

Wikipedia, "Gear", Wikepedia, the free Encyclopedia, last accessed Dec. 1, 2011, 13 pages.

Ikuta et al., "Shape Memory Alloy Servo Actuator System with Electric Resistance Feedback and Application for Active Endoscope", IEEE, dated 1998, 4 pages.

Dumont et al., "A Dynamical Training and Design Simulator for Active Catheters", International Journal of Advanced Robotic Systems, vol. 1, No. 4, dated 2004, 6 pages.

Peirs J. et al., "A Miniature Manipulator for integration in a self-propelling endoscope", dated 2001, 7 pages.

Peirs et al., "Design of an Advanced tool Guiding System for Robotic Surgery", Proceedings of the 2003 IEEE International Conference on Robotics & Automation, dated Sep. 2003, 6 pages.

Shammas et al., "New Joint Design for Three-dimensional Hyper Redundant Robots", Proceeding of the 2003 IEEE/RSJ, Dated Oct. 2003, 6 pages.

Shammas et al., "Three Degrees-of Freedom Joint for Spatial Hyper-Redundant Robots", Mechanism and Machine Theory, dated 2006, 21 pages.

Simaan et al., "A Dexterous System for Laryngeal Surgery", Proceedings of the IEEE, International Conference on Robotics & Automation, dated Apr. 2004, 7 pages.

Slatkin et al., "The Development of a Robotic Endoscope", IEEE, Dated 1995, 10 pages.

Ocrobotics.com, "Snake Arm Robot Technology," last accessed Oct. 23, 2008, 1 page.

European Patent Office, "Office Action" Received in Application No. PCT/GB 2010/001237, dated Jun. 24, 2010, Applicant: Imperial Innovations Limited, 11 pages.

Current Claim in Application No. PCT/GB2010/001237, dated Jun. 2010, 3 pages.

* cited by examiner

JOINT ARRANGEMENT

The present invention relates to an actuatable joint arrangement in particular, although not exclusively, for a two degree of freedom joint. Specific examples of the application of the joint arrangement include actuatable, articulated endoscopes.

Minimally Invasive Surgery (MIS) is typically carried out through natural body openings or small artificial incisions guided by optical or digital viewing devices known as endoscopes. The traditional endoscope employs a series of achromatic doublets for the relay optics. Modern endoscopes more typically utilize much longer lenses. Combined with high quality lenses and miniature solid state camera modules, an endoscope permits the relay of video from the internal anatomy of the patient onto external video devices. This gives surgeons the opportunity to effectively look inside the patient without causing unnecessary injuries. Also, depending on the optics in use, magnification permits examinations in great detail.

MIS achieves its clinical goals with minimal inconvenience to patients, which results in reduced patient trauma, shortened hospitalisation, improved diagnostic accuracy and therapeutic outcome. Although advantageous to patients, the surgeons have to cope with a number of disadvantages in MIS including the loss of depth perception and tactile feedback, increased complexity of instrument control, and difficult collaborative working environment. In MIS, there is also a reduction in the degrees of freedom available to the surgeons due to the use of long, rigid, ergonomically unnatural instruments associated with the "fulcrum effect", necessitating movements by the surgeon's hand in counter-intuitive ways.

Known developments of conventional endoscopes comprise individually actuatable segments cooperatively defining a hollow conduit corresponding to the endoscope. Since the dimensions of endoscopes for surgery involving incisions, such as laparoscopy or arthroscopy, dictate the size of the incision and it is generally desirable to keep incisions in the patient small, it is desirable that the actuating mechanism is arranged in a space-saving manner.

As a safety feature, it is desirable that the actuatable segments are moveable with respect to each other in the event of a failure of the actuating mechanism (for example due to a power failure) such that the endoscope is flexible when the actuators are not powered. This ensures the possibility of removing the endoscope from the body lumen irrespective of its shape in the event of, for example, a power failure. Therefore, it is desirable that the actuators are back-drivable. Further, it is desirable that the resistance to movement of the segments is reduced to facilitate accurate force feedback and transmission along the endoscope. For these reasons, it is desirable that the friction of the components of an actuating mechanism of such articulated segments is reduced.

According to an aspect of the invention there is provided a joint arrangement according to claim 1.

In some embodiments, the joint arrangement includes two joint members which are pivotally linked so that one of the joint members has tendons linked to it such that it is pivotable with respect to the other joint member by pulling on the tendons. A transmission member is disposed around or inside the other joint member and coupled to the tendons to transmit a force through them in order to cause movement of the joint members relative to each other. The transmission member is thus arranged to rotate about an axis lying within the other joint member. The arrangement further comprises a drive means for driving the transmission member to cause it to rotate about the first member in order to transmit the force.

Advantageously, by disposing the transmission member to be rotatable about an axis lying within one of the joint members, a high speed reduction, space-saving force transmission is provided since the diameter of a driven surface of the transmission member is large for a given cross-sectional foot print of the joint arrangement. Moreover, since the transmission member itself rotates around or inside the joint member (as opposed to, for example, next to it if a simple capstan is used to actuate the tendons), tangential friction of the tendons along the circumference of the drive member is eliminated.

In some embodiments, the transmission member defines a spool, including the driven surface or separate from it, on which the tendons are wound such that rotation of the spool in one direction pays out one tendon and takes in the other tendon and rotation of the spool in the other direction takes in the one tendon and pays out the other tendon. The tendons may be provided as a single length of material secured to the spool. In some embodiments, the arrangement comprises a tendon routing arrangement defining an inflection point for each tendon to route each tendon from a direction generally along the spool to a direction generally along the other joint members towards the one joint member. The tendon routing arrangement may include at least one pulley for each tendon portion. It may include two pulleys for each tendon, so that the tendon changes direction twice, which allows force transmission to be improved in some embodiments. Advantageously, the tendons may be attached to the joint member by a resilient attachment such as a compression spring disposed between an end of each tendon and the one joint member to which they are attached to take up any slack in variations of tendon path length as the first and second joint portion pivot relative to each other.

In some embodiments, one end of each tendon portion is attached to the second joint member and another end of each tendon portion attached to the transmission member. One end is thus fixed on the transmission member and the other end is thus fixed on the second joint member. In other embodiments, the tendon portions are slideably secured to the second joint member and one end of each tendon portion is attached to the first joint member and the other end of each tendon portion is attached to the transmission member. One end is thus fixed on the transmission member and the other end is thus fixed on the first joint member. The tendon portion may run to the second joint member and across the second joint member along the pivot and then back to the first joint member. In this way, force transmission to the second joint member can be doubled.

In some embodiments, the inflection points define a line which is off a plane defined by the attachment point on the transmission member/spool, at which the tendons are attached as the transmission member rotates. As a result, the incremental change in the path length as the transmission member rotates varies with the position of the attachment point between the inflection points and the resulting change in the sides of the triangle defined by the three points. This variation is opposite in direction to the variation of the incremental total path length change of the tendons between the inflection points and the second joint member as the sides of the corresponding triangles change and therefore at least partially compensates for the change in the path length. Further, the displacement of the attachment point may result in improved conversion from torque applied to the transmission member to force generated in the tendon (requiring less applied torque for a given tendon force).

In some embodiments, the joint arrangement defines a through-bore when the two joint members are aligned such that, for example, a surgical instrument can be passed through the bore. Advantageously, the drive means are secured, in some embodiments, to an outer aspect of the joint members so as not to intrude into the space provided for the through-bore. Or, the drive means may be disposed within the joint member to provide a smooth outer surface of the joint member.

In some embodiments, the transmission member defines a toothed surface along at least part of its circumference to define a gear and the drive means define a corresponding pinion to mesh with the gear. The transmission member may extend around or inside all of the joint member or only around a part of its circumference. Likewise, the toothed surface may extend over the entire circumferential extent of the transmission member, or only over a part of it to define a sector gear.

In some embodiments, the drive means includes an electric motor secured to the joint member adjacent to the transmission member for driving the transmission member, for example using the pinion mentioned above. A controller may be secured to the joint arrangement for locally controlling the drive means and, in some embodiments, the controller may be addressable by a data bus.

In some embodiments, the joint arrangement is such that the joint-members rotate relative to each other about a longitudinal axis.

In some embodiments, a joint comprises two joint arrangements as described above mounted together such that their respective pivot axes are perpendicular to each other to define a two degree of freedom joint comparable to a universal joint. In some embodiments, the joint comprises a single degree of freedom, for example in a manner similar to the pivot of the medial or distal joint in a finger. In some embodiments, a segmented device comprises a plurality of such joints to define an instrument bore through the joints along the length of the device such that an instrument, for example a surgical instrument, can be passed through the device. Some embodiments provide an endoscope, for example a laparoscope or other endoscope, comprising such a segmented device. Advantageously, the individual joints of the segmented device may be controlled by a common data bus, requiring minimal wiring along the length of the device.

In some embodiments, the second joint member defines a twist lock feature for securing the second joint member to another joint arrangement. This facilitates easy assembly of single or multiple joint devices. The twist lock feature may have complementary male and female features to lock with another identical twist lock feature, maximising flexibility in how joint arrangements can be interconnected and also reducing manufacturing costs due to the same mould being useable for the twist lock feature for all joint arrangement. The twist lock feature may secure to another twist lock feature by virtue of the female feature having an opening which is narrower than the largest width of the male feature perpendicular to the tangential direction of the twist lock feature.

To facilitate maintaining electrical connectivity throughout a segmented device assembled from joint arrangements as described above, the second joint member may include one or more electrical contacts for slidingly engaging corresponding contacts on the other joint arrangement as the twist lock feature is locked. To ensure positive contact, the contacts may be resiliently biased to engage corresponding contacts on another joint arrangement, for example by spring loading. To facilitate the assembly as the joint arrangements are rotated relative to each other for locking, the contacts may have a rounded end for engaging the corresponding contacts on another joint arrangement.

Embodiments of the invention are now described by way of example for the purpose of illustration only and with reference to the accompanying drawings in which.

Figure 1:
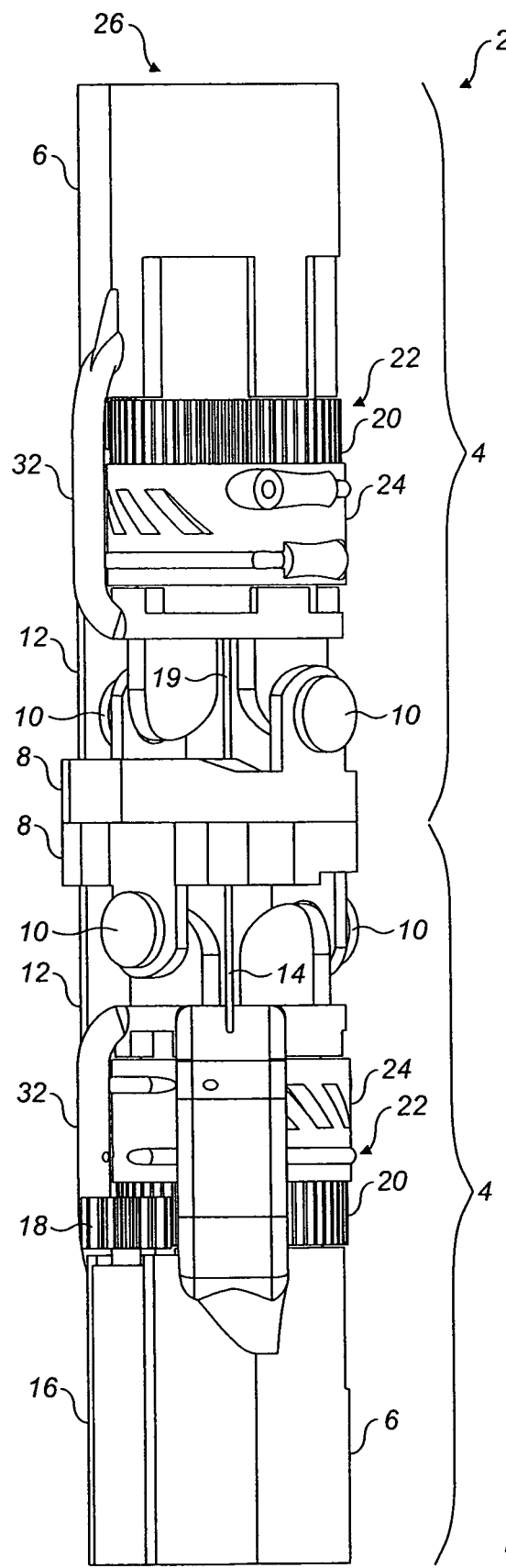
FIG. 1 shows a perspective view of a tendon driven two degree of freedom joint.

With reference to FIG. 1, a two dimensional, universal-type joint 2 comprises two one degree of freedom joint arrangements 4, each comprising a first joint member 6 and a second joint member 8, linked together by a pivot 10 about which the joint members 6, 8 are pivotable with respect to each other. The two joint arrangements 4 are secured to each other at their second joint members 8 such that the respective pivot axes defined by the pivots 10 are perpendicular to each other to provide a two degree of freedom, universal-type joint action. Alternatively, the two second joint members 8 are provided as a unitary item in some embodiments, so that the joint comprises two first joint members 6 linked to a common second joint member 8 which defines two mutually perpendicular pivot axes about which the respective first joint members can pivot with respect to the second joint member.

Figure 2A:
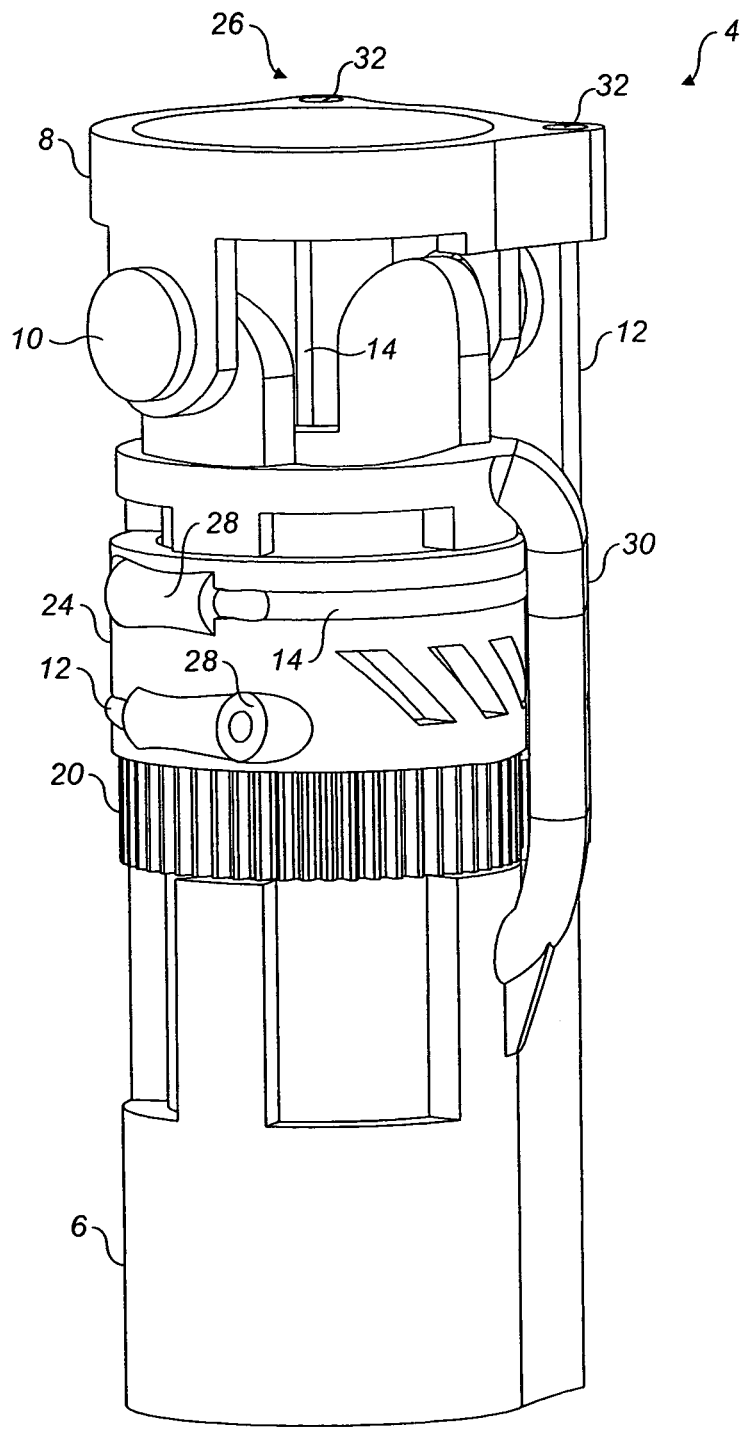
FIGS. 2a and 2b show enlarged perspective views of a lower joint arrangement of the joint in FIG. 1.
Figure 2B:
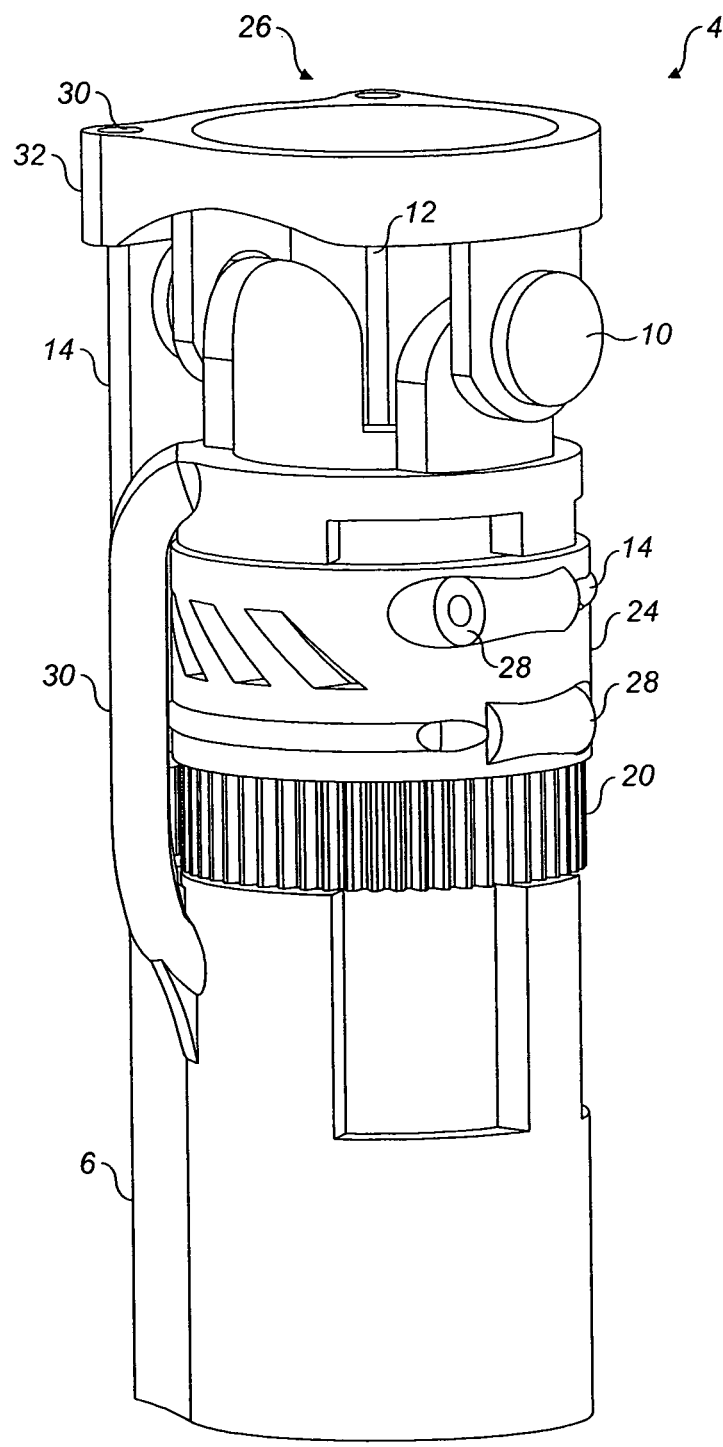
Figure 3:
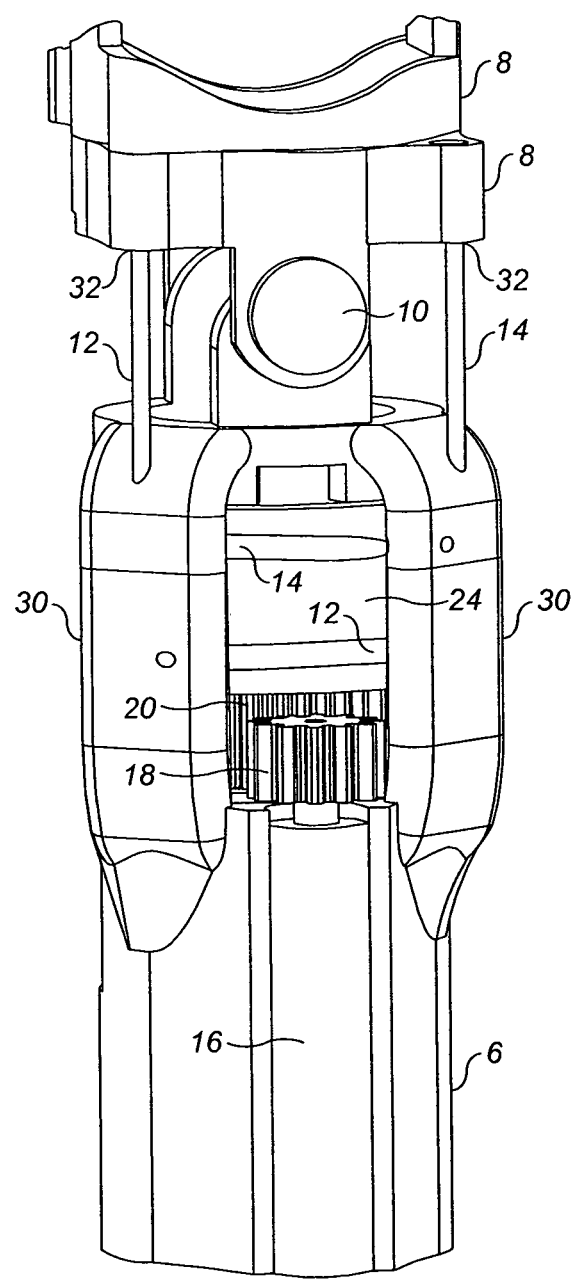
FIG. 3 shows yet a further enlarged view of this joint arrangement, focussing on the interaction between the drive means and a transmission member.
Figure 4:
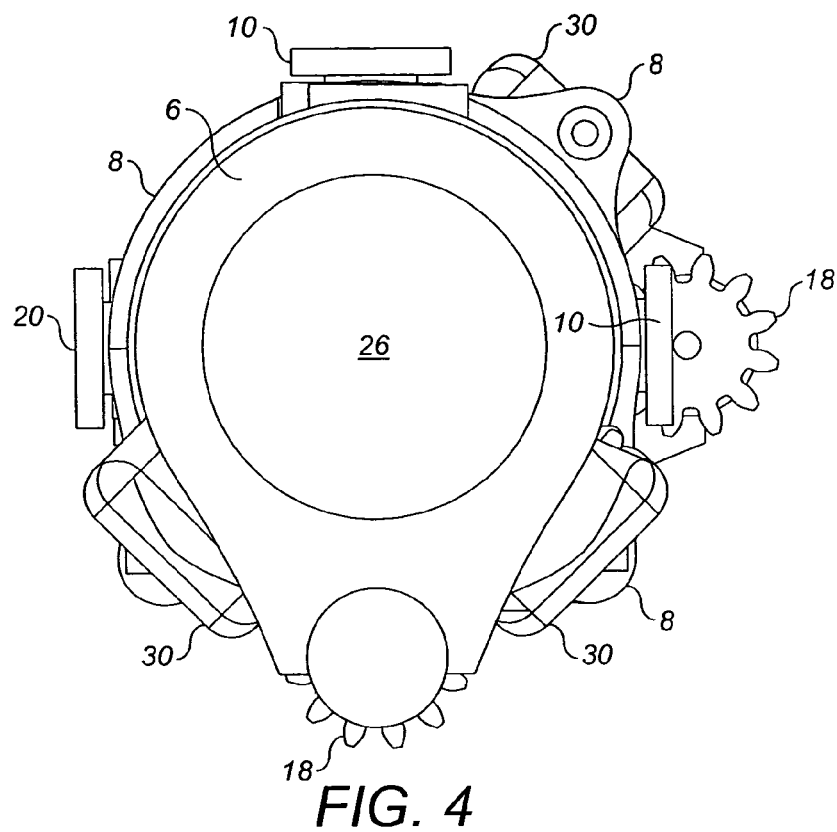
FIG. 4 shows a top-down view of the joint arrangement.
Figure 5:
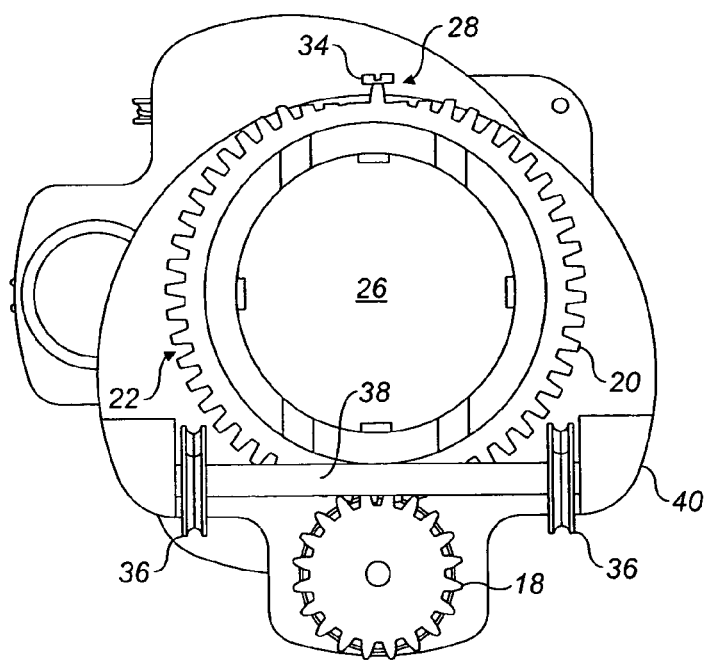
FIGS. 5 to 12 illustrate alternative transmission members and tendon routings.
Figure 6:
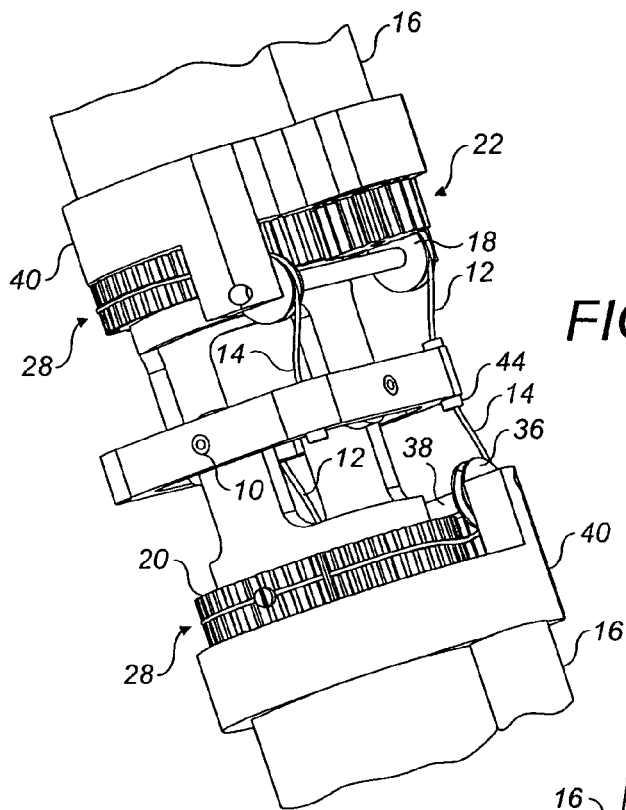
Figure 7:
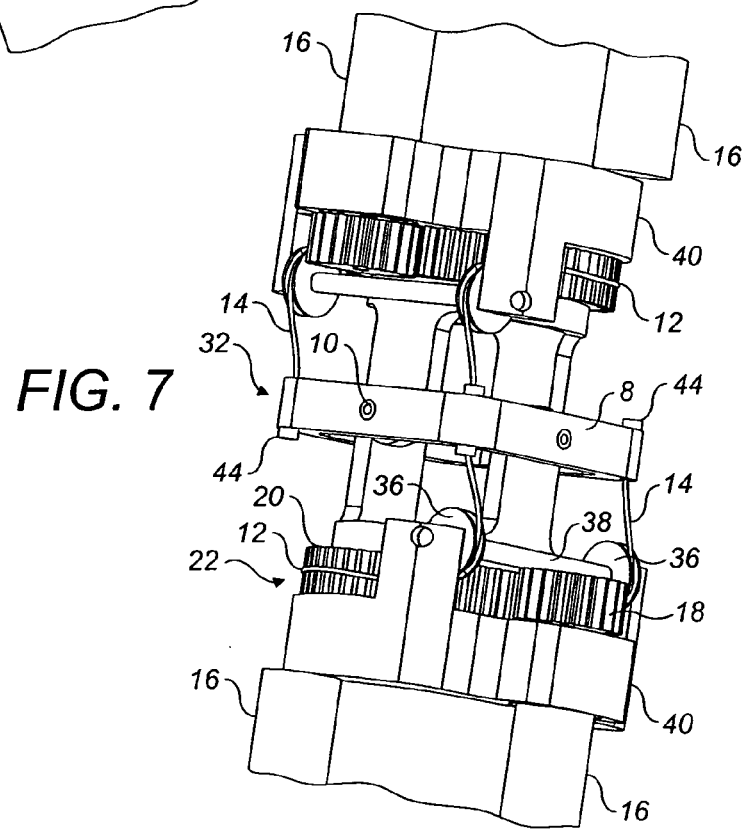

With reference to FIGS. 2a and b, 3 and 4, a first and a second tendon 12, 14 are secured to the second joint member of the joint arrangement 4. The tendons 12, 14 are secured to the second joint member at locations on either side of the pivot 10 so that tension in the first tendon 12 pivots the second joint member in one direction, for example clockwise, and tension in the second tendon 14 pivots the second joint member 8 in the other direction, for example counter-clockwise.

An electric motor 16 is secured to the first joint member 6 on an exterior aspect of the joint member 6. In some embodiments, the electric motor is a brushless DC motor. The rotor of the motor is coupled to a pinion 18 which engages a toothed surface 20 of a transmission member 22.

The transmission member 22 is generally cylindrical and disposed around a diameter of the first joint member 6, so that it is rotatable with respect to the first joint member 6 about an axis lying longitudinally within the first joint member 6. The transmission member 22 is supported on the first joint member 6 by a suitable bearing, for example a sliding bearing such as defined by two low friction material coated, for example PTFE coated, surfaces, roller bearings or ball bearings in various embodiments.

The toothed surface of the pinion 18 engages the toothed surface 20 so that rotation of the pinion 18 by the motor 16 causes rotation of the transmission member 22 around and about the first joint member 6. This provides a reduction gear having a maximum diameter for a given diameter of the first member 6, reducing the speed of the transmission member 22 driven by motor 16, driving the tendons 12 and 14, as described below. Additionally, in some embodiments, the pinion 18 is coupled to the motor 16 by a further reduction stage.

The transmission member 22 further defines a spool 24 to which the tendons 12 and 14 are secured. In some embodiments, the spool 24 defines respective channels for guiding the tendons 12 and 14. The tendons are routed around the spool from an attachment point 28 circumferentially around the transmission member 22 to a tendon guide 30 and then to an anchor point 32 on the second joint member 8. The force transmitted to the second joint member can be increased by reducing the diameter of the spool 24, for example making it smaller than the diameter of the toothed or driven surface of the transmission member 24 (which is applicable for all transmission members having a separate spool portion).

In some embodiments, the toothed surface 20 and spool 24 are spaced axially along the transmission member 22. The spool defines two axially displaced tracks for the tendons 12 and 14, allowing the tendons to overlap axially as they are routed from their respective attachment points 28 to their respective tendon guides 30. The tendon guides 30 are secured to the first joint member bridging the axial extent of the transmission member so that each tendon passes underneath the tendon guide 30 of the other tendon before reaching its own guide member.

Each tendon guide 30 defines a channel for guiding the respective tendon 12, 14 from a tangential direction along the spool to a direction generally along the first joint member 6 towards the anchor point 32 on the second joint member 8. This allows a tangential force generated by rotation of the transmission member 22 to be transmitted along tendons 12, 14 and to convert the force into a force generally along the direction of the joint members by guiding a change of direction of the tendons 12, 14 to cause pivoting of the second joint member 8 about its pivot 10.

The pivots 10, motors 16 and pinions 18, transmission member 22, tendon guides 30 and anchor point 32 extend radially outwards from a surface of the joint members, which defines a longitudinal through-bore 26 extending through the first and second joint members 6, 8 along the entire length of the joint 2. Advantageously, this allows an instrument to be passed through the through-bore, which is particularly advantageous in a segmented device comprising a plurality of joints 2, described in detail below. Because the features described above extend radially outward from the joint members, the through-bore 26 is not cluttered by obstacles to the smooth passage of such instruments or other objects.

As will be appreciated, the maximum cross-section of the through-bore through the joint 2 is achieved when the joint is in an aligned position, whereas pivoting of the joint members relative to each other provides for, in effect, a bent conduit.

With reference to FIGS. 5 to 12 embodiments having alternative transmission members and tendon routings are now described. Specifically, with reference to FIGS. 5 to 8, in some embodiments the toothed surface 20 of the transmission member 22 also provides the spool 24 and the tendons 12, 14 are secured to the toothed surface by a fixation member 34, such as a screw. The tendons 12, 14 are routed directly on the toothed surface from the fixation member 34 to a respective pulley 36 on either side of the transmission member 22. The pulleys 36 are rotatably secured on a common axis 38 which is in turn held in place by a collar 40 which also secures the motor 16. From the pulleys 36, the tendons 12, 14 are routed to the anchor point 32 on either side of the pivot 10.

In some embodiments, the end of the tendon is resiliently secured at attachment point 28 and/or anchor point 32. Specifically, in some embodiments a compression spring is disposed between an end of each tendon 12 and 14 and the respective anchor points 32 on the second joint member 8, such that a tension on the tendons 12 and 14 will compress the respective compression spring. The length of the tendons 12 and 14 is adjusted such that the compressions springs are in a partially compressed configuration when the first and second members 6 and 8 are aligned such that any slack in the tendons 12 and 14 as the first and second joint members 6 and 8 pivot with respect to each other is taken up by a decompression of the compression springs. This arrangement serves to accommodate small changes in tendon path length as the joint members pivot relative to each other, thereby maintaining constant tension during the tendons travel and reducing backlash in the joint.

In some embodiments, the tendons 12 and 14 may be anchored to the second joint member 8 by a spring between the respective ends of the tendon and the anchor points 32 such that a resilient balancing force is created by stretching the springs.

In some embodiments, the resilient attachment is achieved by a block of resilient material such as a polymer material rather than a spring or the tendons themselves may provide the resilience to keep the tension during pivoting of the joint members.

Figure 8:
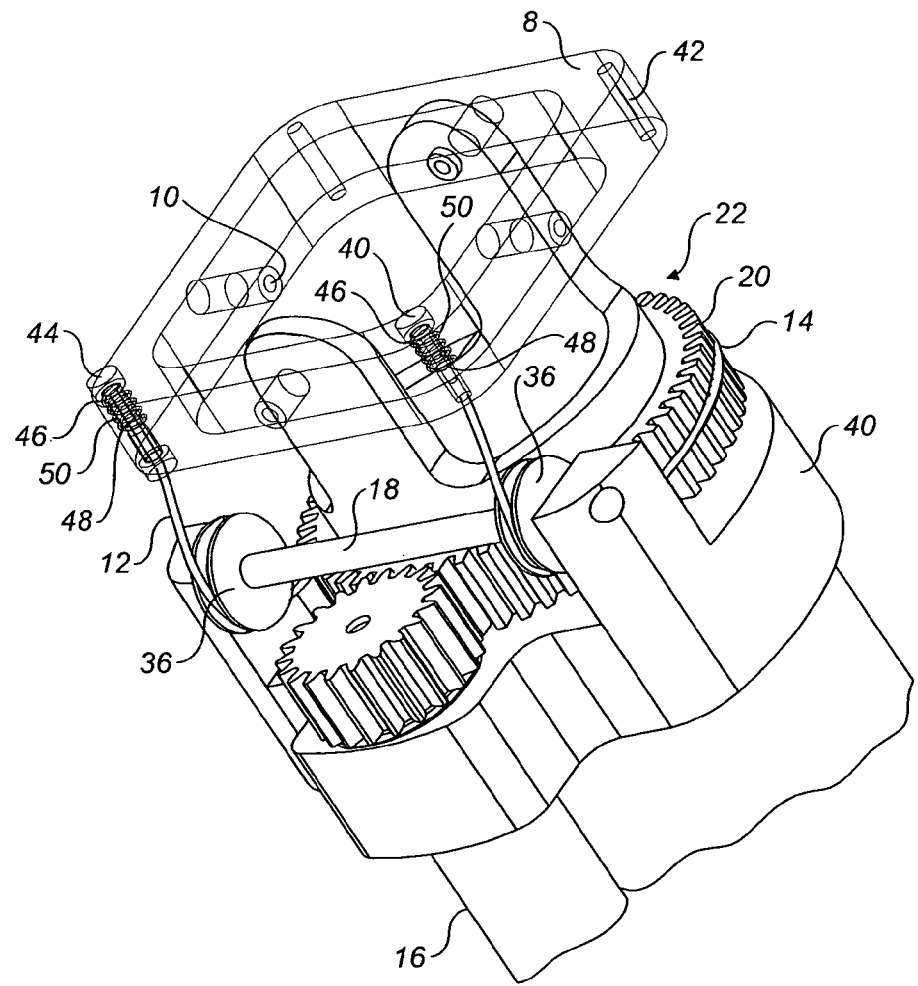

Specifically with reference to FIG. 8, the second joint member 8, in some embodiments, defines a through bore 42 in each corner for accommodating the tendon 12. The tendon 12 passes through the through bore 42 and is secured to a stopper 44 at its free end. The stopper 44 and through bore 42 define respective shoulders 46, 48 which face each other and a compression spring 50 is disposed between the shoulders to provide the resilient path lengths compensation described above. Some or all of the stoppers 44 may in turn provide a through bore so that another tendon 14 from a further first joint member 6 can travel through the through bore and be secured with a further stopper 44 on an opposite aspect of the second joint member 8.

In some embodiments, now described with reference to FIGS. 9 to 11, the transmission member surrounding the first joint member 6 (having an outward facing toothed surface) is replaced with an internal transmission member 22 rotatably secured within the first joint member 6 and having an inward facing toothed surface 20 and an outward facing glide surface 52 disposed against an inner surface of the first joint member 6. To reduce friction, in some embodiments, the glide surface 52 is coated with low friction material. Other means of reducing friction such as ball bearings or roller bearings are used in other embodiments.

Figure 9:
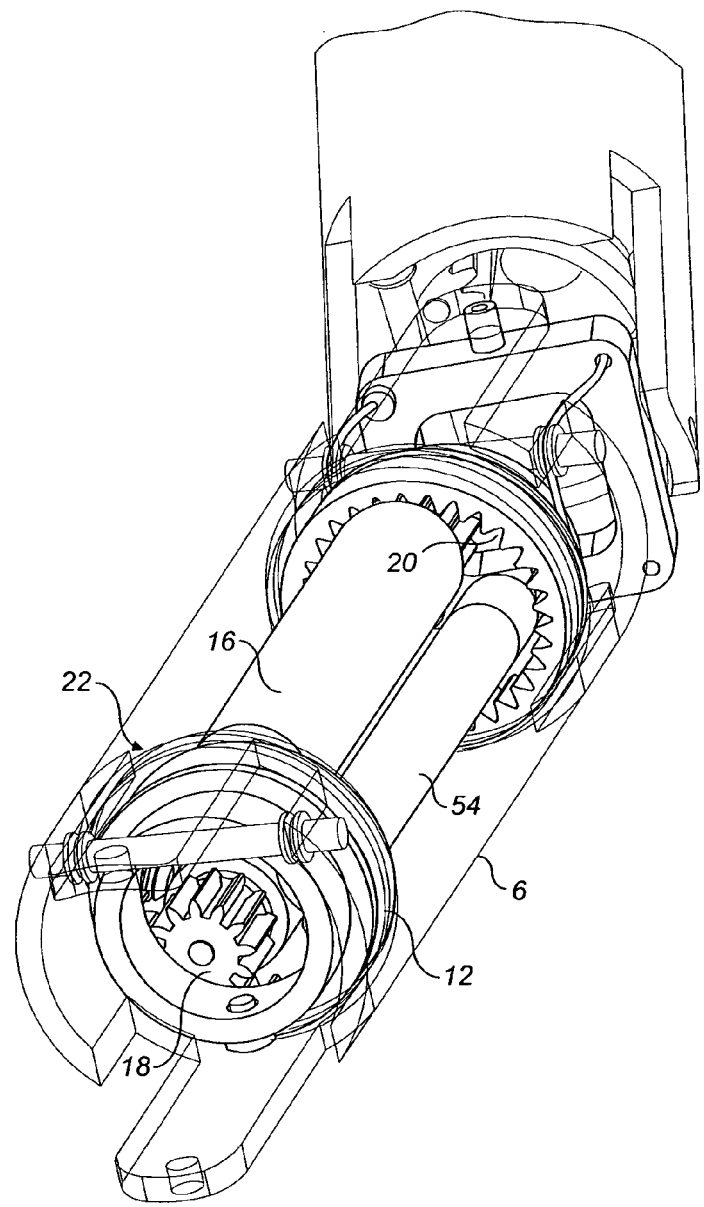
Figure 10:
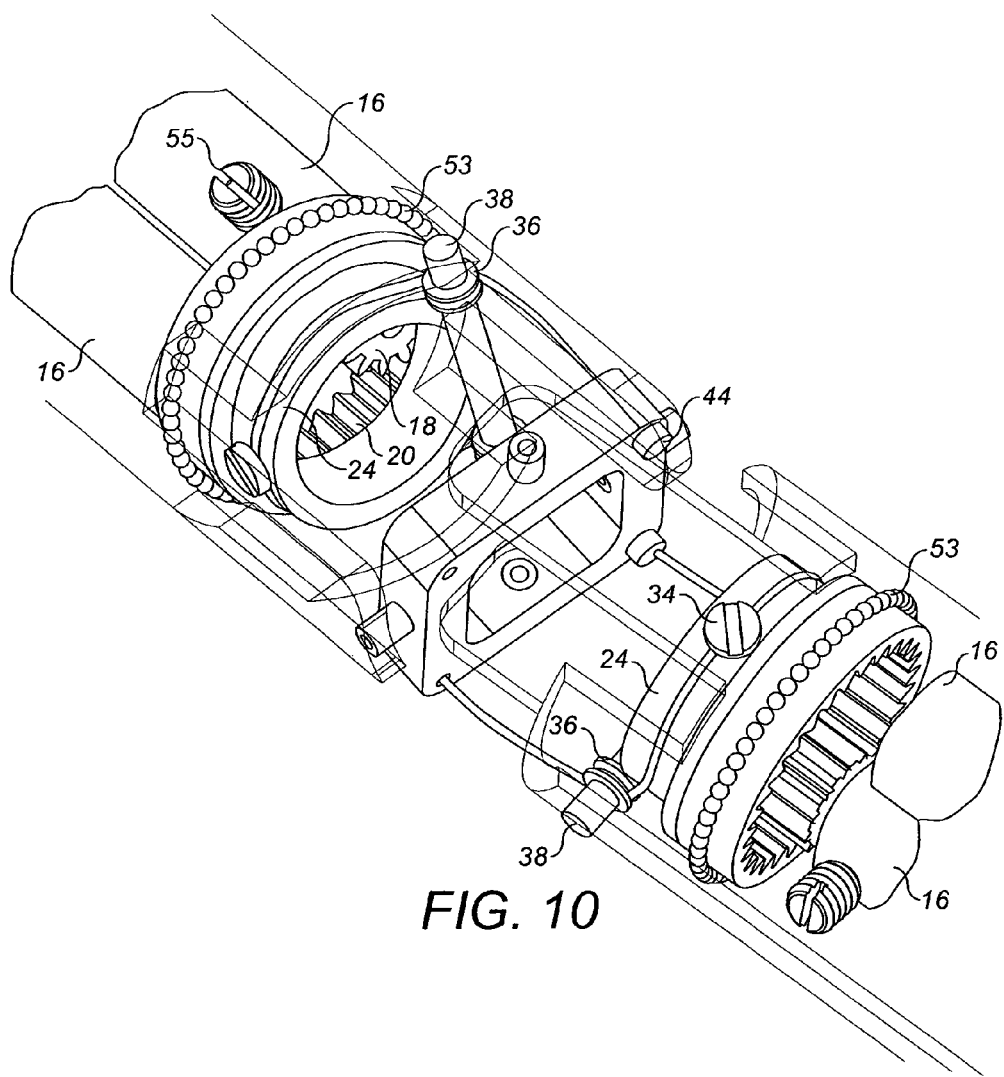
Figure 11:
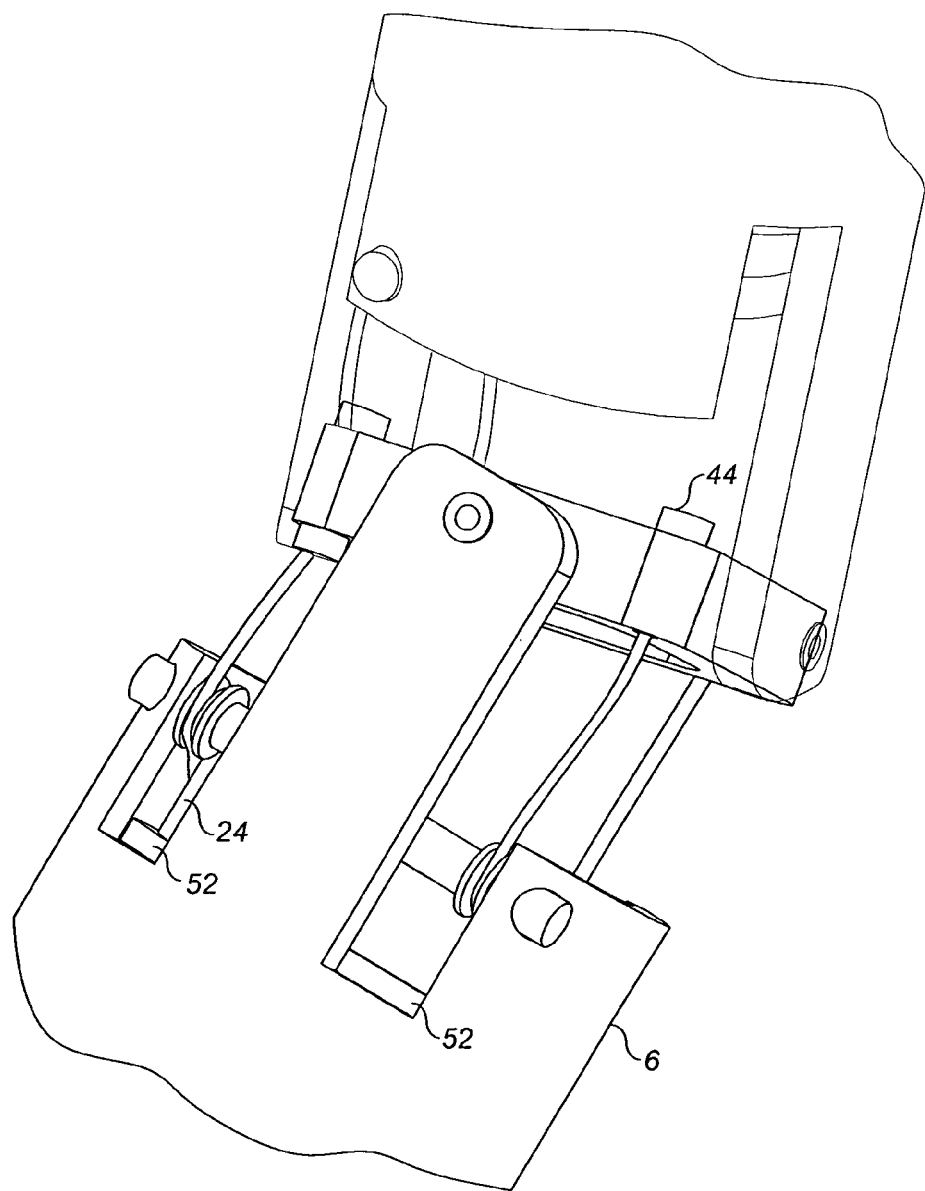

As can be seen from FIGS. 9 and 10, in which several components, including the joint members 6 have been rendered transparent, the motor 16 is now placed within the joint member 6 and the pinion 18 meshes with the toothed surface 20 from the inside. The through bore 26 is thus filled with two motors 16 (one to actuate a single axis at each end of the joint unit) of the first joint members 6 leaving a reduced space for the instrument channel which is defined by a hollow tube 54 disposed through the through bore 26.

Between the first joint members 6, the tubes 54 are joined by a flexible tube which passes between first joint members 6 through the second joint member 8 to connect adjacent tubes 54 (not shown). Alternatively, the tubes 54 may not be connected between first joint members or the instrument channel may simply be defined by the remainder of the through bore 26 left by the two motors.

With reference particularly to FIG. 10, the low friction material glide surface 52 is replaced or augmented with ball bearings 53 in some embodiments. In some embodiments, the motors 16 are held in place by grub screws 55.

The tendon routing is similar to that in the embodiments described above with reference to FIGS. 5 to 8 in that the tendons are routed around a spool on a common axle secured to the first joint member 6 to spring loaded anchor points but, like the embodiments described above with reference to FIGS. 1 to 4, the transmission member 22 defines a separate spool 24 on which the tendons run on either side of the fixation member 34 to the pulleys 36. As described above, the force transmitted to the second joint member can be increased by reducing the diameter of the spool 24, for example making it smaller than the diameter of the transmission member 24.

While the internal arrangement of the toothed surface 20, motors 16 and pinion 18 reduces the space available for an instrument channel, conversely, it provides a smooth outer surface for the first joint members 6 and allows the overall diameter of the joint arrangement to be reduced, which may be preferable in some applications.

Figure 12:
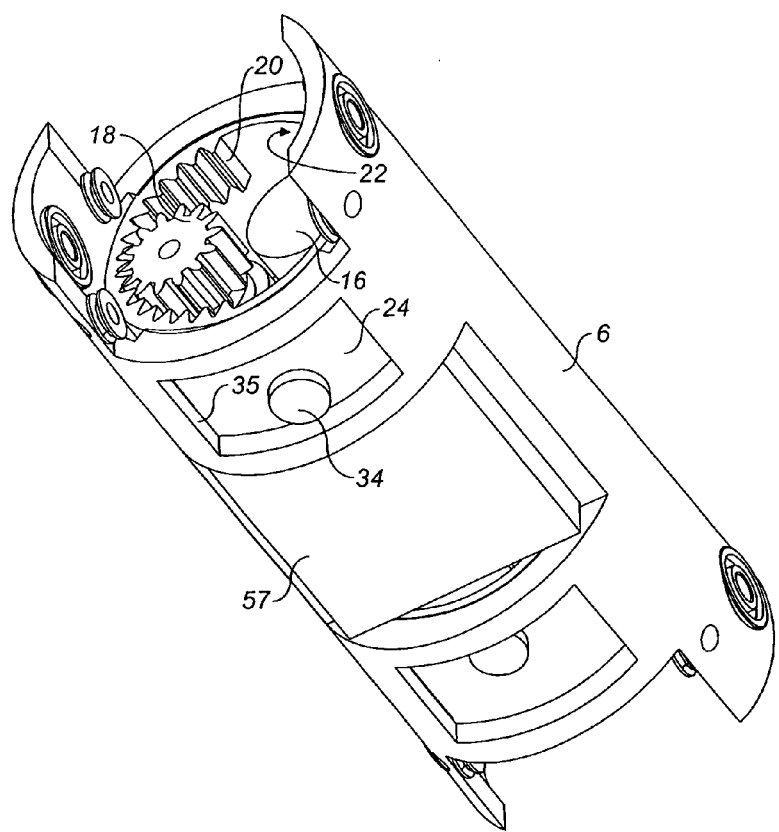

With reference to FIG. 12, in some embodiments, the toothed surface 20 extends only around part of the transmission member 22. In embodiments where the transmission member is internal, as shown in FIG. 12, this enables a space saving to be achieved by disposing the motors 16 in an overlapping configuration with a respective transmission member 22 which is not driven by the motor 16 using the space liberated by the partial absence of the (inner) toothed surface 20. This allows the first joint member 6 to be made relatively more compact, both longitudinally and transversely.

Further longitudinal space savings are achieved in some embodiments by disposing the spool 24 transversely adjacent the toothed surface 20 on an outer aspect of the transmission member 22, rather than longitudinally adjacent. The fixation member 34 can be accessed and is free to move in a window 35 and the tendons are free to move inside a recessed space (not shown) inside the first joint member 6.

As further illustrated in FIG. 12, the first joint member 6, in some embodiments, comprises a recess for accepting a microprocessor 57 for processing sensor data and controlling the motors 16, as described in more detail below.

Figure 13:
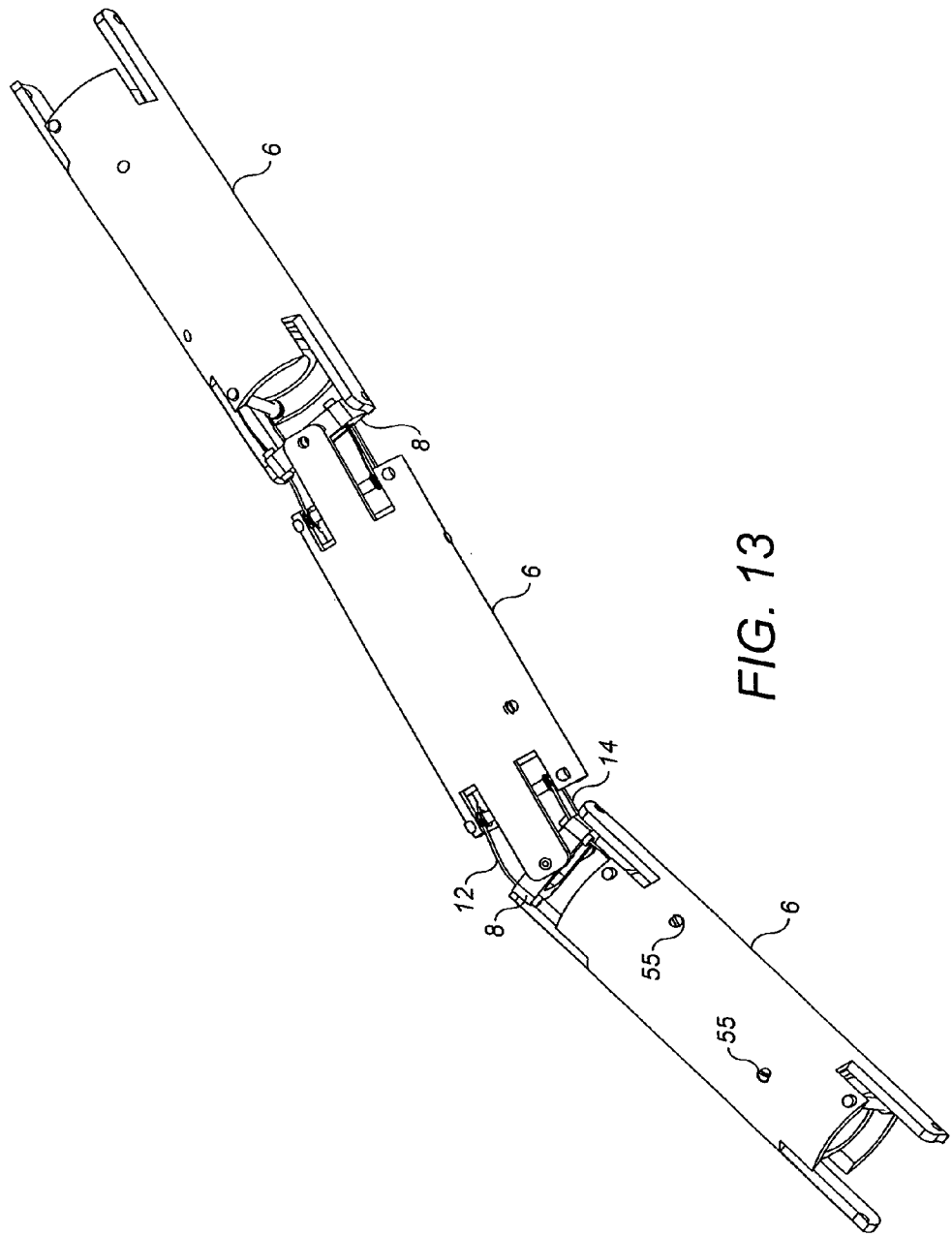
FIG. 13 illustrates a combination of three joint members to form two linked universal joints.

With reference to FIG. 13, a 4 degree of freedom chain of segments comprising first and second joint members as described above comprises three first joint members 6 each comprising a motor and corresponding driving arrangement for each end of the joint member 6 so that each joint member 6 controls one degree of freedom at each of its ends. Adjacent joint members 6 are rotated by 90° with respect to each other to provide perpendicular degrees of freedom at the intervening second joint members 8.

In the embodiment depicted in FIG. 13, the degrees of freedom defined at each end of the joint members 6 are parallel. However, in alternative embodiments, the respective degrees of freedom of each joint member may be rotated with respect to each other by 90 degrees. In these embodiments, the joint members 6 are chained in the same orientation to define two perpendicular degrees of freedom at each second joint member 8. While FIG. 13 depicts a chain of first joint members 6 as described above with reference to FIGS. 9 to 11, illustrating the smooth outer surface of the resulting chain, the specific arrangement of the joint members 6 is readily interchangeable without loss of generality. Equally, one or more of the first joint members 6 may be pivotally connected directly to an adjacent first joint member to define a 1 degree of freedom finger joint.

It will be noted that various embodiments have been described with reference to FIGS. 5 to 13, which alter features of the embodiments described with reference to FIGS. 1 to 4, such as the second joint member 8, the transmission member 22, the guide 30/pulley 36, path compensation/spring loading, internal or external arrangement of the motor and drive arrangement and the arrangement of the motor itself. It will be understood that the features are to some extent independent of each other and that any one or more of these can feature in any appropriate combination with the features described above to replace corresponding features or in addition to existing features.

Figure 14:
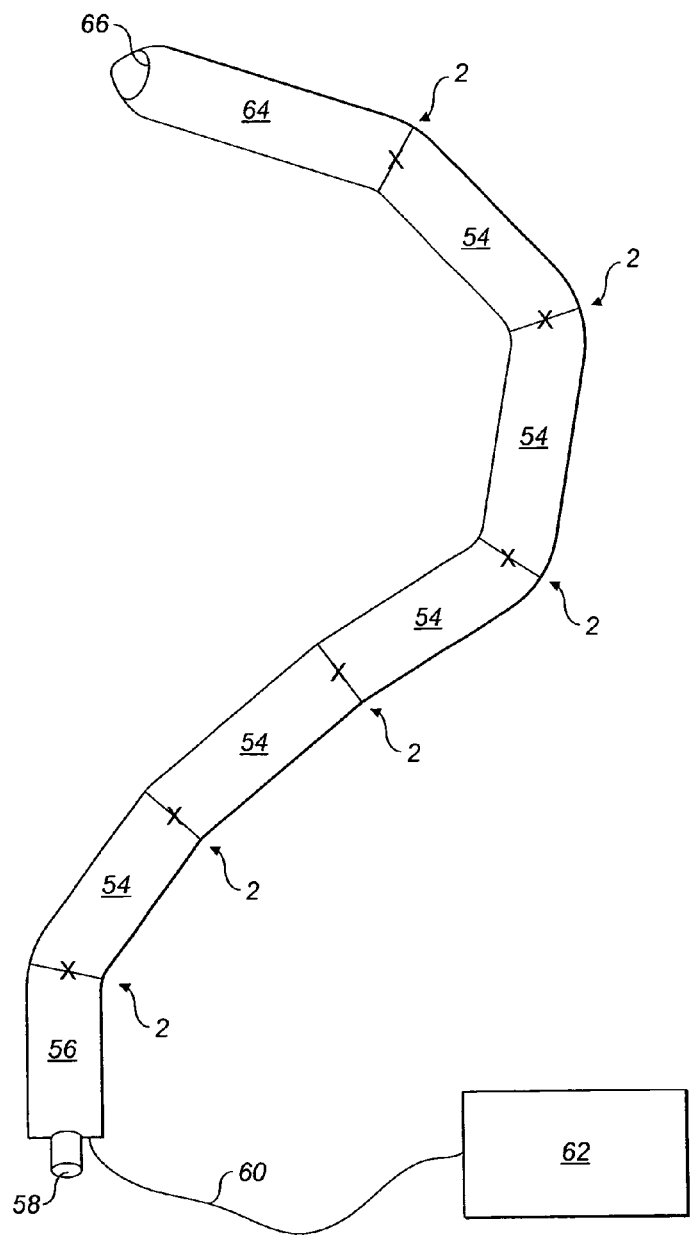
FIG. 14 illustrates a segmented device comprising joints as described below with reference to FIGS. 1 to 13.
Figure 15:
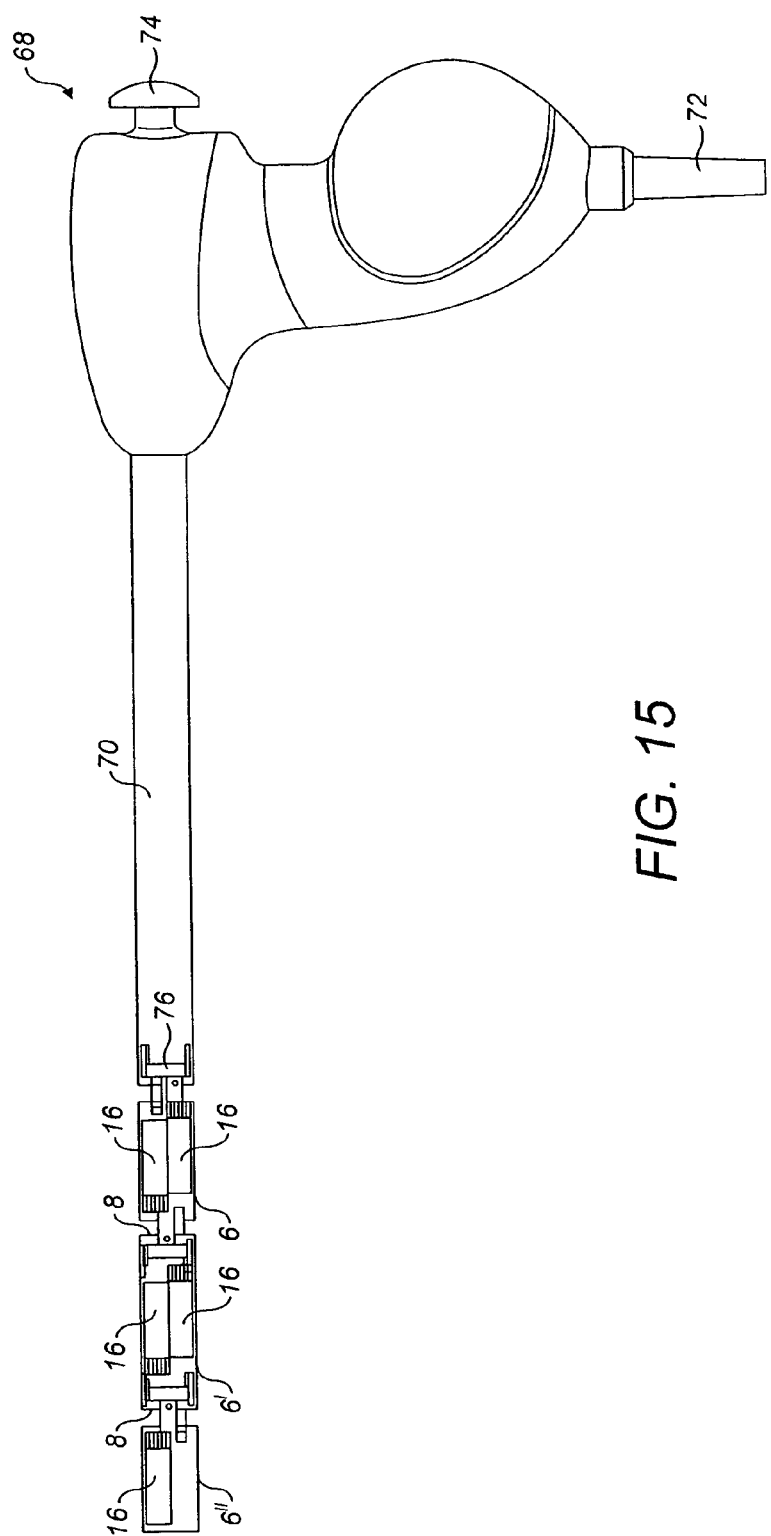
FIG. 15 illustrates a hand-held segmented device.

With reference to FIG. 14 an endoscope device comprising a plurality of joints 2 as described above is now described. The device comprises a plurality of hollow segments 54 each comprising a joint 2 as described above at each end, having two degrees of freedom indicated by the "X" in FIG. 14. The device provides a hollow, flexible conduit for delivering an instrument through the conduit through an enclosed space along a tortuous route. A device having N such segments will have 2 (N−1) degrees of freedom.

At a proximal end of the device a proximal interface member 56 is coupled to its adjacent segment 54 and provides an instrument port 58 and a bi-directional data connection 60 for transmitting sensor data from the device to a control unit 62 and control signals from the control unit 62 to the device. In some embodiments, the data connection is unidirectional, transmitting control signals only.

At the distal end, the device comprises a distal end member 64. The end member 64 defines an aperture 66, through which an instrument advancing through the hollow interior of the device gains access to an enclosed space into which the device is inserted. The distal end member 64 may further comprise sensors such as optical sensors to collect data of the end member's environment and provide visual feedback.

One or more of the following signals are provided from the device to the control unit 62: joint angles for each degree of freedom of each segment 54, rotor position data from each motor 16, representative of joint angles, supply current for each electric motor, representative of joint load (where electric motors are position controlled); and any other signals from additional sensors present on the device.

In some embodiments, each segment 54 includes an embedded processor which pre-processes data from sensors provided on each segment and sends processed joint orientation and load information to the control unit 62 over a data-bus. In other embodiments, not every segment has its own processor but only every other segment comprises an embedded processor handling sensed and control signals for two adjacent segments. Yet further embodiments have an embedded processor every $3^{rd}$, $4^{th}$, etc, segment in a similar fashion. The control unit 62 further sends control signals to each of the segments 54. In embodiments in which each segment 54 (or a subset of segments) comprises a processor addressable over a data-bus, the control signals are high level signals such as a desired joint load and/or joint orientation for each degree of freedom or an alternative representation, such as yaw and pitch angle as the two degrees of freedom.

In some embodiments in which a local processor is provided for each (or every other, etc) segment 54 transmission and sensor and control data is over a data-bus, and only power lines are needed in addition to the data bus.

The device may have between ten and thirty segments, or even more than that, to define a device with a length of between 500 to 1400 mm. The hollow conduit inside the device may vary between 1 mm to 12 mm. The maximum outer diameter may be 18, preferably 12 mm. Naturally, the device may have less segments and/or different dimensions, for example as described below.

In one specific embodiment, a micro-brushless DC motor having a maximum torque of 10.6 mNm and a maximum current of 6 to 54 mA at a maximum voltage of 3 to 5V is used. An embedded controller comprises a 16 bit RISC processor with 10 KB RAM, 12 bit analogue to digital converter for processing sensor signals, a 12 bit digital to analogue converter for actuating the electric motor and two UART serial connections for communication with the controller 62.

In some embodiments, a hand held segmented device comprises a grip portion 68 connected at one end to a connecting rod 70 and at the other end to a cable port 72 for accepting a data cable for connecting the hand held device to a data processor such as a computer. The grip portion comprises a multi directional control button 74 for controlling the device. At a free end, the connecting rod 70 is connected to a first joint member 6 attached to an attachment boss 76 to define a one degree of freedom finger joint. The first joint member 6 is connected to a further joint member 6' by a 2 degree of freedom joint and the further joint member 6' is connected to yet a further joint member 6" by a further two degree of freedom joint, giving a total of 5 degrees of freedom for the device. More joints can be added to increase the total degrees of freedom of the device. Any of the devices described above can also be used in a master-slave setup, where the control unit and the end effectors are linked through digital control, through either wired or wireless configurations.

As briefly discussed above, the geometry of the joint arrangement results in differences in the sum of path lengths of the tendons 12 and 14 as the joint pivots to one side, which can give rise to undesirable backlash and instability. One solution, resiliently tensioning the tendons, has been discussed above and another, geometric approach is now described. It will be understood that these approaches can be used in combination or each on its own. The geometry of the joint arrangement and its effect on the tendon path lengths will be discussed in detail below with reference to FIGS. 16 and 17 but, in overview, the path lengths difference arises because the portions of the tendon paths on each side of the joint between the guide arrangement or pulley and the second joint member do not add up to a constant total path length as the joint pivots, so that one of the tendons will slacken as the joint pivots as one tendon is paid out more than the change in the corresponding tendon path.

Figure 16:
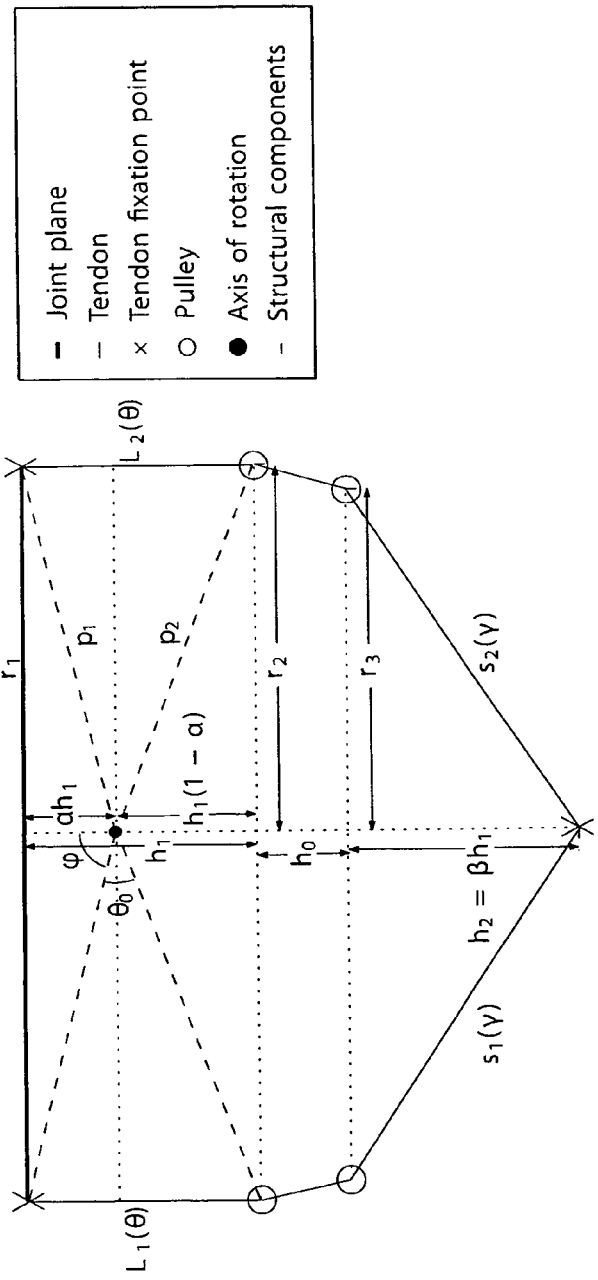
FIGS. 16 to 18 illustrate a geometric path length compensation design.
Figure 17:
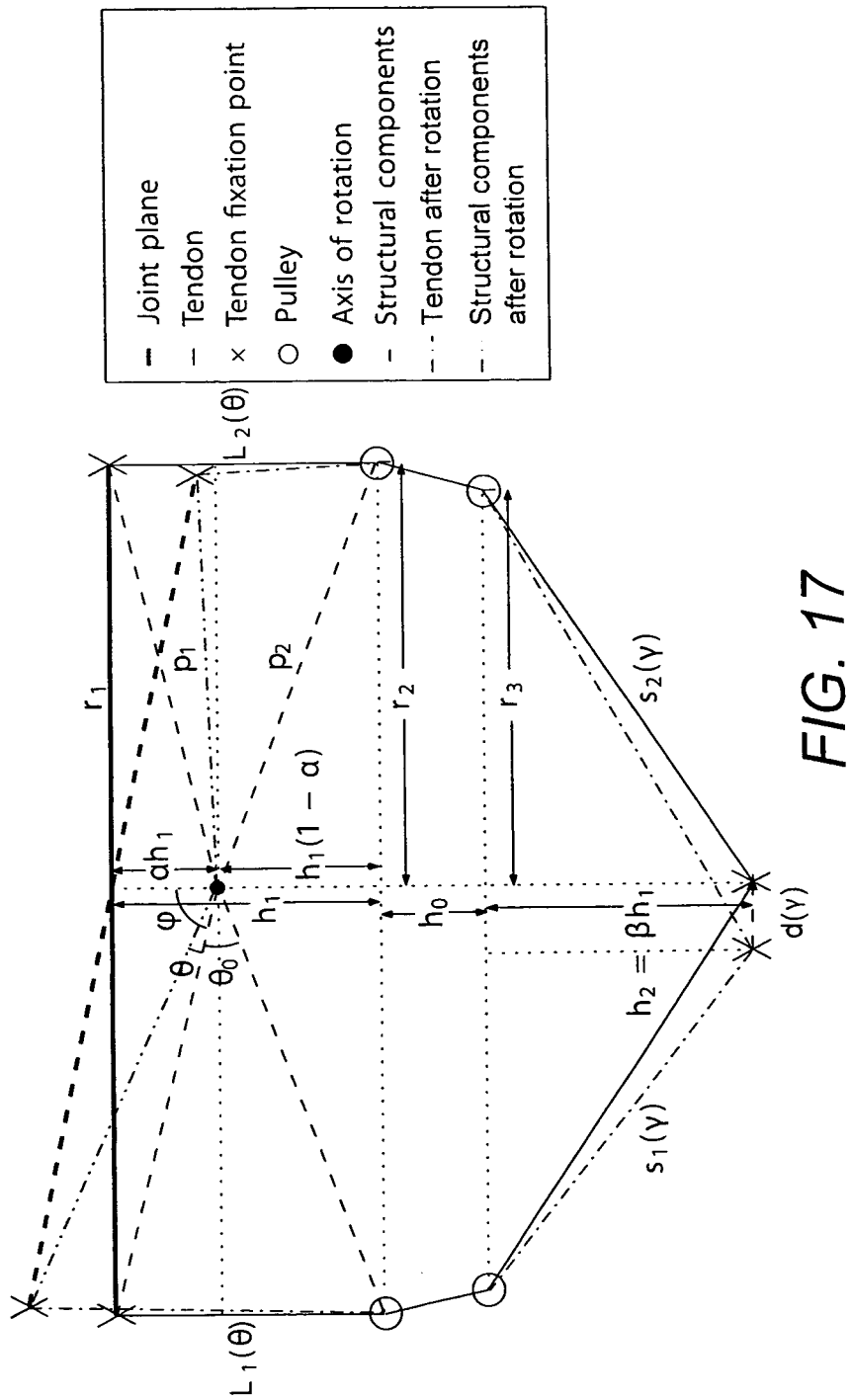

When the tendon attachment point 28 on the transmission member is in line with the pulleys 36 the path lengths between the attachment point and a respective pulley 36 on each side sum to a constant length as the attachment point 28, travels on an arcuate trajectory in a plane containing the pulleys (projected onto a straight line between the pulleys in FIGS. 16 and 17). By displacing the attachment point from alignment with the pulleys, for example away from the pivot point, so that it travels in a plane off a line joining the inflection points defined by the pulleys, a path length difference for the tendon between the pulleys and the attachment point can be achieved which at least partially compensates for the path lengths difference between the pulleys and the second joint member so that tendon slack and backlash can be reduced. This will now be described in detail with reference to FIGS. 16 and 17.

In FIGS. 16 and 17, the bold line represents the plane of the joint (the second joint member 8, width $2r_1$) while the solid line corresponds to the total tendon length connecting the second joint member 8 to the attachment point 28 on the transmission member (marked with an X). A first set of upper pulleys is positioned at a distance $h_1$ below the plane of the joint, a width $2r_2$ apart, while a second set of lower pulleys is located at a distance $h_0$ below the plane of upper pulleys, a width $2r_3$ apart. This is a more general case of the embodiments described above, for which $h_0=0$ and $r_2=r_3$ (the value of $h_0$ does not affect the subsequent analysis). The attachment point 28 (X) of the tendon on the transmission member 22 is placed at a distance $h_2$ below the plane of the lower pulleys. The position of the axis of rotation of the joint is defined by the parameter $\alpha$, which represents the fraction of the total length $h_1$ defining the distance between the plane of the joint and its axis of rotation. The distance between the axis of rotation of the joint and the line connecting the upper pulleys is therefore given by $h_1(1-\alpha)$. Different values can be assigned to $r_1$, $r_2$ and $r_3$.

The following analysis assumes that the radius of the surface of the transmission member 22 on which the tendons run is $r_3$. The more general case can readily be derived by the person skilled in the art.

Figure 18:
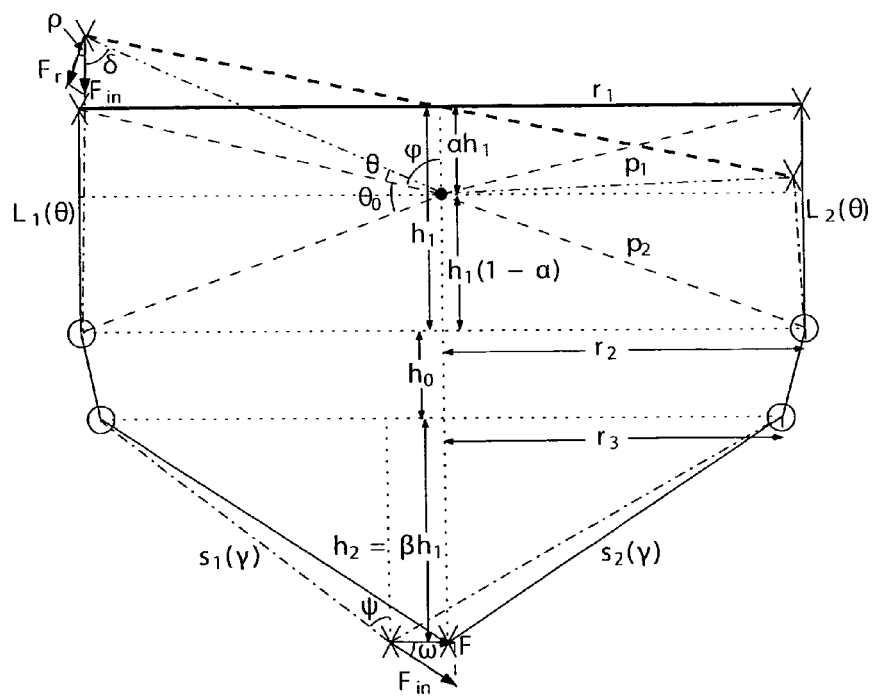

FIG. 16 shows a straight configuration of the joint arrangement and FIG. 17 shows the configuration of the joint after a rotation about its axis of an angle ?, corresponding to a displacement d of the attachment point on the circumference of the transmission member, projected on a plane defined by the pulleys perpendicular to the axis of rotation (the plane of the paper in FIGS. 16 to 18). The following quantities, illustrated in FIGS. 16 and 17 are useful to define:

$$p_1 = \sqrt{(\alpha h_1)^2 + r_1^2}$$

$$p_2 = \sqrt{h_1^2(1-\alpha)^2 + r_2^2}$$

It is also useful to define the angle $\theta_0$ given by:

$$\theta_0 = \arccos\left(\frac{p_1^2 + p_2^2 - ((r_1 - r_2)^2 + h_1^2)}{2 \cdot p_1 \cdot p_2}\right)$$

Note that in general $p_1 > 0$ and $p_2 > 0$.

From FIG. 17, the lengths of the tendons connecting the joint to the upper pulleys vary when the joint rotates clockwise (?>0) according to:

$$L_1 = \sqrt{p_1^2 + p_2^2 - 2 \cdot p_1 \cdot p_2 \cdot \cos(\theta_0 + \theta)}$$

$$L_2 = \sqrt{p_1^2 + p_2^2 - 2 \cdot p_1 \cdot p_2 \cdot \cos(\theta_0 - \theta)}$$

so that the corresponding elongation of the left tendon is:

$$\frac{\partial L_1}{\partial \theta} = \frac{p_1 \cdot p_2 \cdot \sin(\theta_0 + \theta)}{\sqrt{p_1^2 + p_2^2 - 2 \cdot p_1 \cdot p_2 \cos(\theta_0 + \theta)}}$$

and the shortening of the right tendon is:

$$\frac{\partial L_2}{\partial \theta} = -\frac{p_1 \cdot p_2 \cdot \sin(\theta_0 - \theta)}{\sqrt{p_1^2 + p_2^2 - 2 \cdot p_1 \cdot p_2 \cos(\theta_0 - \theta)}}$$

As shown in FIG. 17, a joint rotation of an angle $\theta$ corresponds to rotation through an angle $\gamma$ of the transmission member which results in the displacement d shown in the figure. The lengths of the tendons connecting the attachment point on the transmission member with the lower pulleys vary with the rotation of the transmission member according to:

$$s_1 = \sqrt{\left(\frac{\pi}{2}-\gamma\right)^2 r_3^2 + h_2^2}$$

$$s_2 = \sqrt{\left(\frac{\pi}{2}+\gamma\right)^2 r_3^2 + h_2^2}$$

where $h_2$ is defined as a fraction of the height $h_1$ through the parameter $\beta$ ($h_2 = \beta h_1$).

When the transmission member rotates, the relationship between $\theta$ and $\gamma$ can be defined given the geometry specified in FIGS. 16 and 17, noting that the path length for the tendon that drives the joint during the rotation does not change by definition since the physical length of the tendon does not change and the driving tendon is under tension as it drives the joint. For example, when the joint rotates clockwise the right tendon (length $L_2+s_2$) is driving the joint and the variation of $L_2$ is, by definition, equal to the variation of $s_2$ (i.e. $\Delta L_2 + \Delta s_2 = 0$), since the physical length of the tendons is constant and the right tendon is tensioned during clockwise rotation.

As discussed above, when the transmission member drives the joint in a clockwise direction the path length for the right tendon does not change, so the overall change in path length is due to the left tendon. In order to avoid backlash the path length for the left tendon should also remain constant, that is the shortening of $s_1$, ($\Delta s_1$), should be equal to the lengthening of $L_1$ ($\Delta L_1$), i.e., $\Delta s_1 + \Delta L_1 = 0$. A similar condition needs to be satisfied to reduce backlash when the transmission member drives the joint in an anti-clockwise direction and the left tendon is tensioned driving the joint while the path length of the right tendon changes, that is the shortening of $s_2$ ($\Delta s_2$) and the lengthening of $L_2$ ($\Delta L_2$) should be equal ($\Delta s_2 + \Delta L_2 = 0$) to avoid backlash. Considering that the length of the right and left tendon paths is the same in an initial configuration when $\theta=0$ ($s_1+L_1=s_2+L_2$), the path length change may be optimised such that $s_1+L_1$ is as close as possible to $s_2+L_2$ during any rotation (clockwise or counter clockwise) of the transmission member to minimise backlash.

Displacement of the tendon attachment point will result in a change of the tendon path length due the variation of $s_1$ and $s_2$ as described above. Backlash can be reduced by setting those parameters discussed above which are dictated by design constraints to a fixed value and optimising the remaining parameters, as is well known in the art, to minimise an appropriate cost function. Examples of cost functions to be minimised over all rotation angles to reduce backlash are the variance of the total path length $L_1+L_2+s_1+s_2$, $(\Delta L_1+\Delta s_1)^2 + (\Delta L_2+\Delta s_2)^2$, $(L_1+s_1-L_2-s_2)^2$, or any other cost function which captures the difference between the total path lengths on each side of the joint, or the cost function as specified below.

In order to ensure the feasibility of the mechanism it may be necessary to limit the range of rotation of the transmission member. As is clear from e.g. FIGS. 5 to 12, the attachment point 34 must clearly not be allowed to travel past ±90° to ensure proper tensioning of the tendons. For example, rotation of the transmission member is limited to between ±45° while the joint rotates in the range ±30°. This constraint will be considered in the optimization described below.

The described parameter based model of the joint can also be used to compute the force transmission efficiency between the motor turning the transmission member and the tendon pulling the joint plane. FIG. 18 shows the rotated joint configuration with variables relevant to the force transmission, where F is the force exerted on the tendon by applying torque to the transmission member, $F_{in}$ is the corresponding input force transmitted by the tendon at its anchor point to the joint plane and $F_r$ is the resultant force generating the torque $t_r$ about the pivot axis of rotation with $t_r = F_r D$, where D is the distance from the anchor point of the tendon on the joint plane to the pivot axis of rotation (the filled circle in the figures), which corresponds to $p_1$ in FIGS. 16 and 17. In some specific embodiments, the transmission member includes a ring gear and F therefore can also be termed the gear force.

According to the diagram in FIG. 18, the input force on the tendon is:

$$F_{in} = \frac{F}{\cos(\omega)}$$

where:

$$\omega = \frac{\pi}{2} - \psi$$

and $\psi$ depends on the displacement of the transmission member through:

$$\psi = \arctan\left(\frac{(\pi/2+\gamma)r_3}{h_2}\right)$$

From these equations it can be seen that cos (?) decreases as $h_2$ increases and, as a result, a smaller force F generated by a torque on the transmission member is required to provide the same $F_{in}$. Thus, offsetting the attachment point of the tendon provides increased force transmission as some of $F_{in}$ (the vertical component) is provided irrespective of the torque on the transmission member.

Consequently, in embodiments which employ path length compensation as described above, a locating feature is provided to prevent axial movement of the transmission member 22 relative to the first joint member 8 in response to the vertical force component of $F_{in}$. In some embodiments, this is achieved by accommodating a locating feature or ridge of the transmission member in a corresponding circumferential recessed channel or groove in the inner or outer aspect (as the case may be) of the first joint member 8.

The resultant force rotating the joint is related to the force $F_{in}$ exerted on the joint at the tendon anchor point through the angle $\rho$:

$$F_r = F_{in} \cos(\rho)$$

Which in turn depends on the angle:

$$\delta = \arccos\left(\frac{L_1^2 + p_1^2 - p_2^2}{2 \cdot L_1 \cdot p_1}\right)$$

through the relation $$\rho = \left|\frac{\pi}{2} - \delta\right|$$

An optimization algorithm to find an optimised mechanical design is aimed to minimize the backlash (range of unconstrained rotation in a fixed angular position resulting from the uncompensated path length changes) and maximize the transmission efficiency when delivering the motor torque to the joint plane. Any suitable optimisation or search technique can be applied, for example such as those provided by commercial packages such as MATLAB®.

In some embodiments, the six variable parameters of the joint design described above are collected in the vector $x=[r_1, r_2, r_3, \alpha, \beta, h_1]$. The total shortening/elongation of the tendon path length during the joint rotation is calculated as:

$$\frac{\partial L_{tot}}{\partial \theta} = \frac{\partial (L_1 + L_2 + s_1 + s_2)}{\partial \theta} = \frac{\partial L_1}{\partial \theta} + \frac{\partial L_2}{\partial \theta} + \frac{\partial s_1}{\partial \theta} + \frac{\partial s_2}{\partial \theta}$$

and the value of x that minimizes its variation range on the interval $-30° \leq \theta \leq +30°$ is found. Upper and lower bound values of x are also fixed. The optimisation thus can be summarised as follows:

$$\min_x \left\{ f(x) = \max\left(\frac{\partial L_{tot}}{\partial \theta}\right) - \min\left(\frac{\partial L_{tot}}{\partial \theta}\right) \right\}$$

$$x_{lb} \leq x \leq x_{ub}$$

Furthermore, in order to achieve adequate torque transmission efficiency, the following constraints are introduced:

$\tau_r \geq 4.5$ mNm $-30° \leq \theta \leq +30°$ $\tau_r(\theta=-30°)=\tau_r(\theta=+30°)$ where $t_r$ is the torque about the pivot point of the joint plane for a gear force F=1N due to a torque applied to the transmission member and the last constraint ensures that the same amount of torque is available at the extreme values of the range of rotation of the joint. This is desirable because having significantly different levels of torque available at different angular displacements of the joint could result in a device incorporating the actuated joint potentially being unable to perform a cantilever lift at one position but have no problem at another. The results of a number of optimisation runs are now described with reference to FIGS. 19 to 42D with:

$x_{lb}=[3.5,3.5,3.5,0,0,4]$ and $x_{ub}=[5.5,5.5,5.5,1,1,6]$ for all calculations. It will be understood that the corresponding joint designs do not necessarily represent global minima of the cost function, so that different optimisation algorithms and different starting conditions can result in different designs. The following examples are therefore included for the purpose of illustration only.

With reference to FIGS. 19 to 24D optimisation results for a design constrained to have $r_2=r_3$ with the remaining parameters allowed to vary (corresponding to the arrangement of the first and second joint members as in FIGS. 1 to 4), is now described. A design found by an optimisation search is illustrated graphically in FIG. 19 and the design parameters x can readily be derived therefrom.

Figure 19:
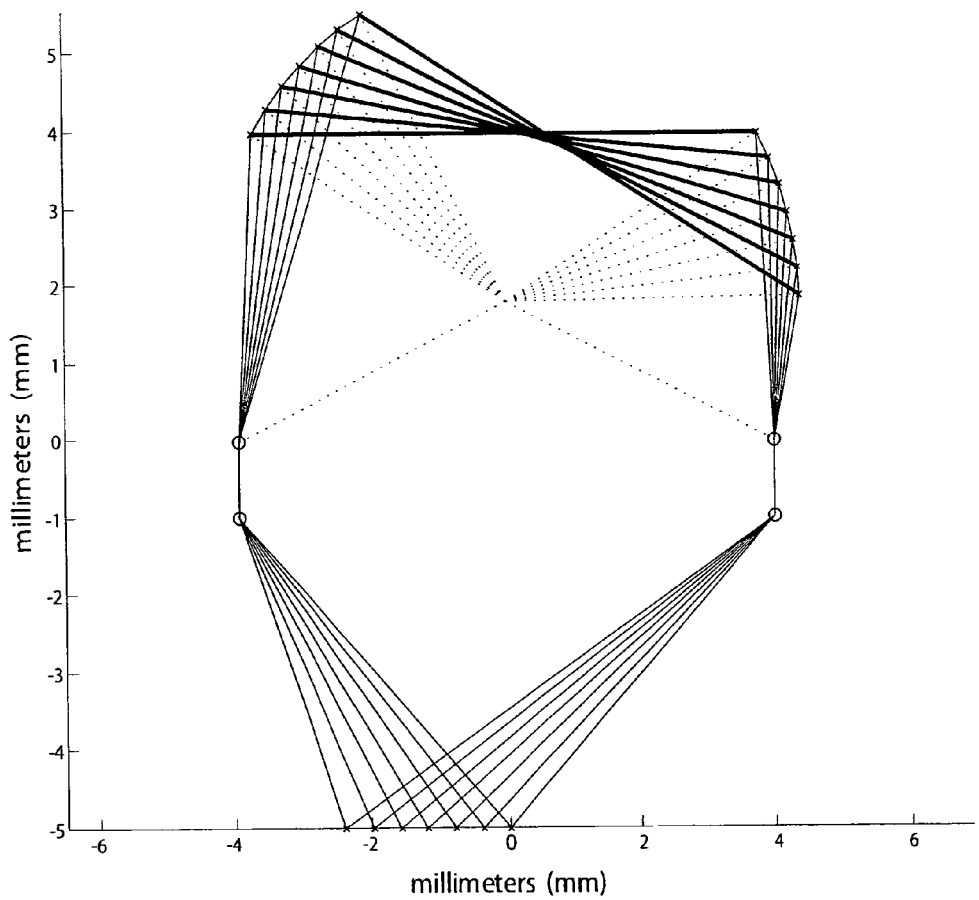
FIGS. 19 to 24D illustrate a specific path length compensation design corresponding to the embodiments of FIGS. 1 to 4.
Figure 20:
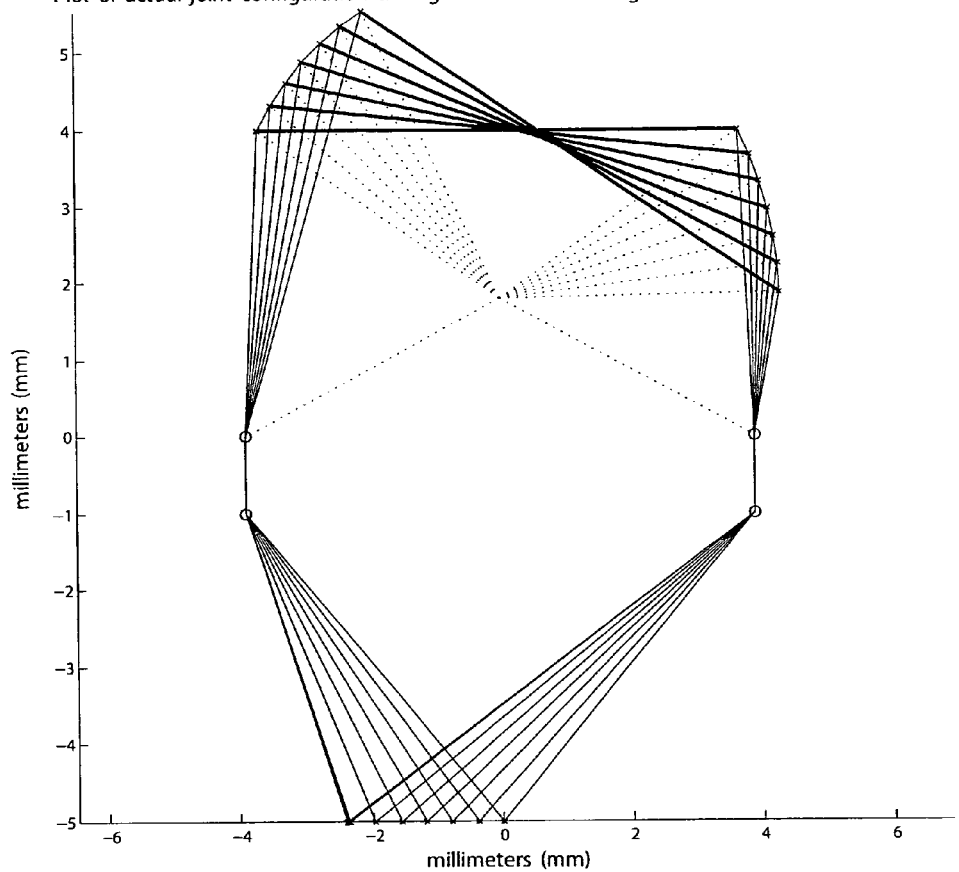
Figure 21:
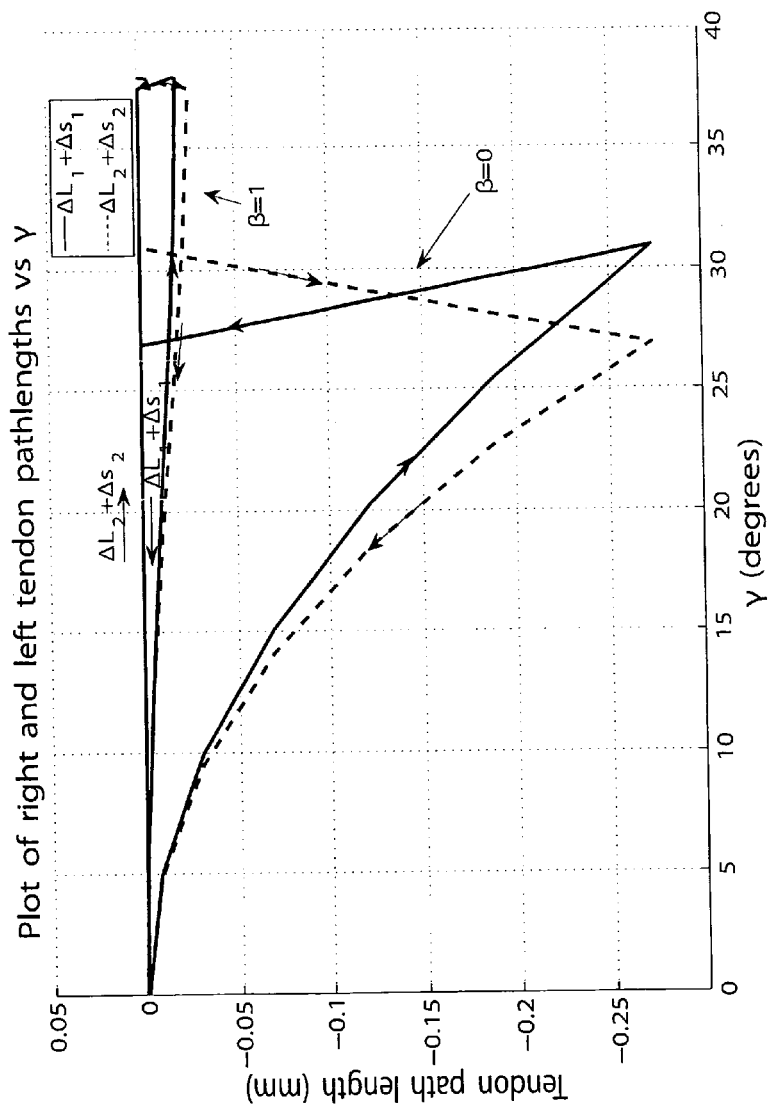

FIG. 19 schematically illustrates the movement of the second joint member and the tendon attachment point on the transmission member for a clockwise rotation of the joint, together with the corresponding tendon paths, while FIG. 20 illustrates the movement of the second joint member for an anti-clockwise rotation of the joint. During the anti-clockwise rotation a small (relative to the case where $\beta=0$, see below) displacement of the transmission member occurs without the joint plane moving, resulting in a corresponding relatively small backlash angle as shown in FIG. 21, which shows the variation in path length of the right and left tendon (with the path length $s_1+L_1=s_2+L_2$ at $\theta=0$ subtracted) during the overall rotation as a function of the transmission member rotation angle $\gamma$.

As is apparent, the path length of the right tendon remains constant during clockwise rotation ($\Delta L_2+\Delta s_2=0$), while the path length of the left tendon varies, causing backlash at the end of the rotation range. When the transmission member rotates anti-clockwise, the backlash has to be recovered before the left tendon becomes tensioned again and can drive the joint rotation. During this time the path length of $s_1$ and $s_2$ changes, while the joint does not rotate so $L_1$ and $L_2$ remain constant. When $\Delta L_1+\Delta s_1=0$ the anti-clockwise rotation of the joint starts and while the path length of the left tendon remains constant the path length of the right tendon changes. The backlash angle therefore corresponds to the amount of transmission member rotation needed to reach $\Delta L_1+\Delta s_1=0$. For comparison, FIG. 21 shows the optimised case and the case with $\beta=0$, which corresponds to positioning the attachment point in a transverse plane comprising the line connecting the lower pulleys. As is apparent, the backlash is reduced of about ten times when the attachment point is displaced.

Figure 22:
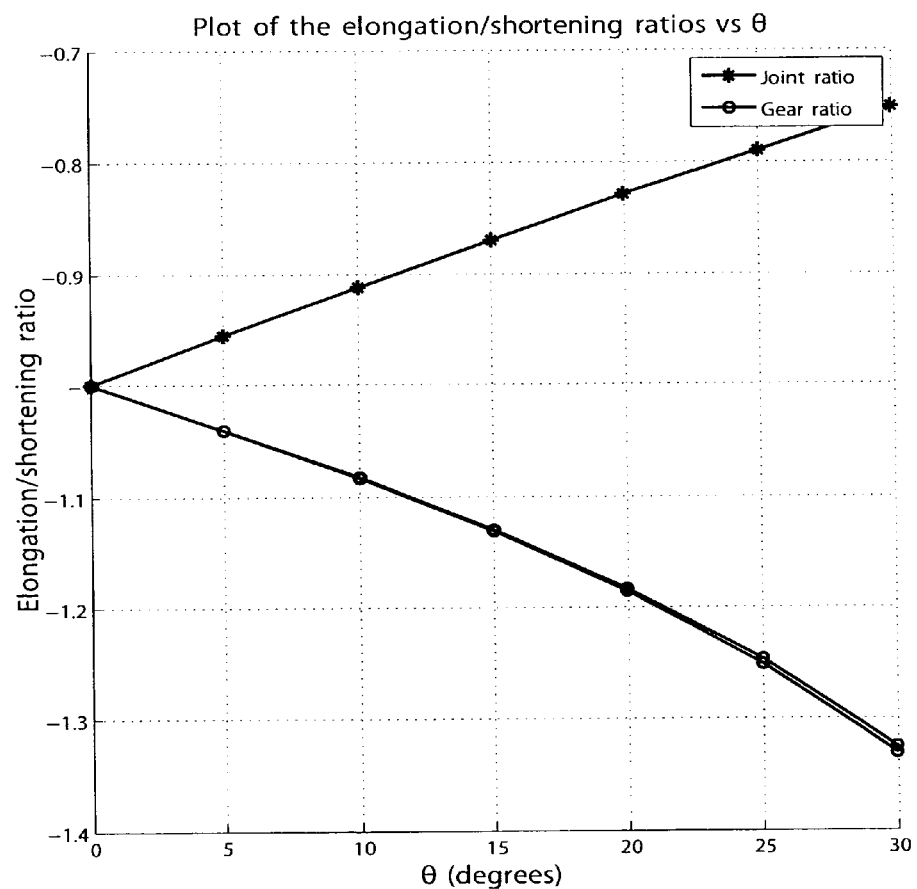
Figure 23:
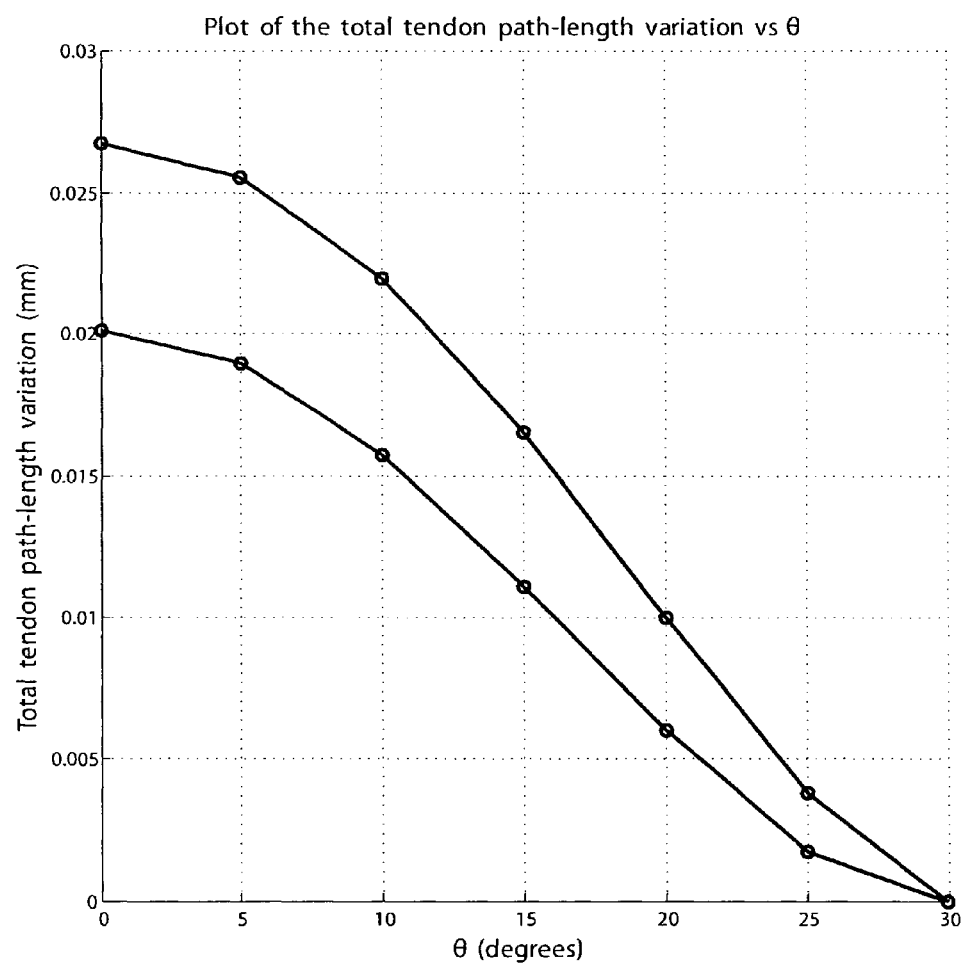
Figure 24A:
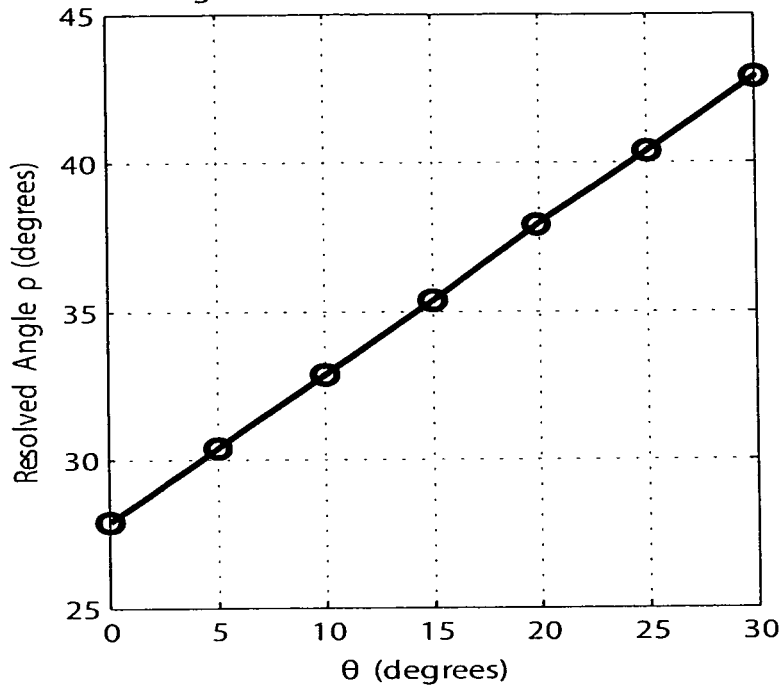
Figure 24B:
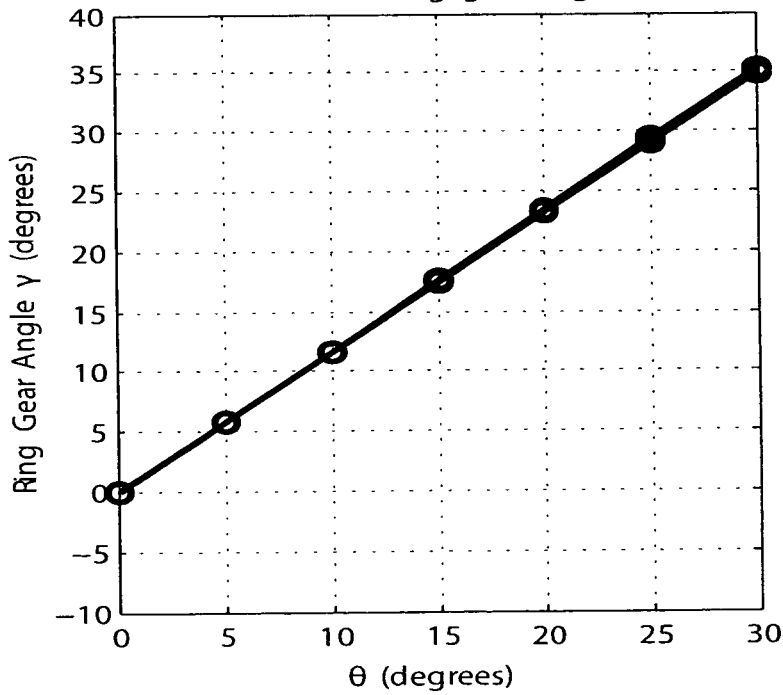
Figure 24C:
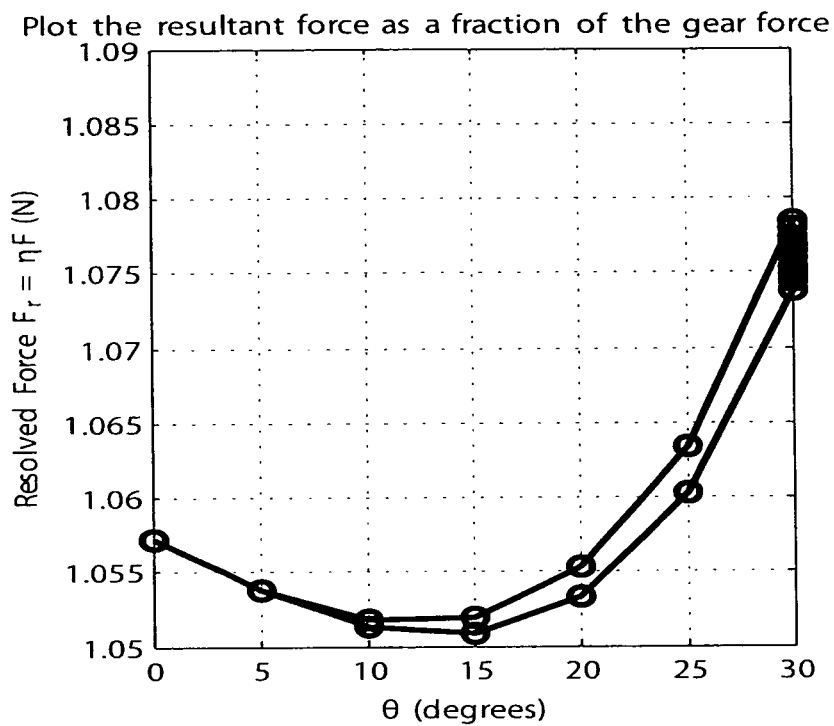
Figure 24D:
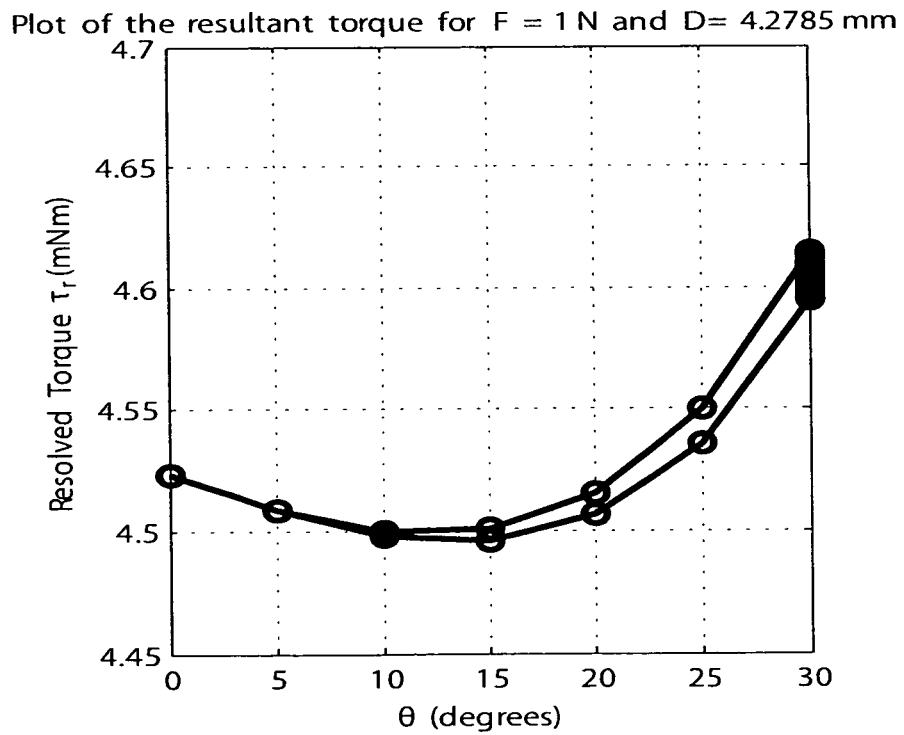
Figure 25:
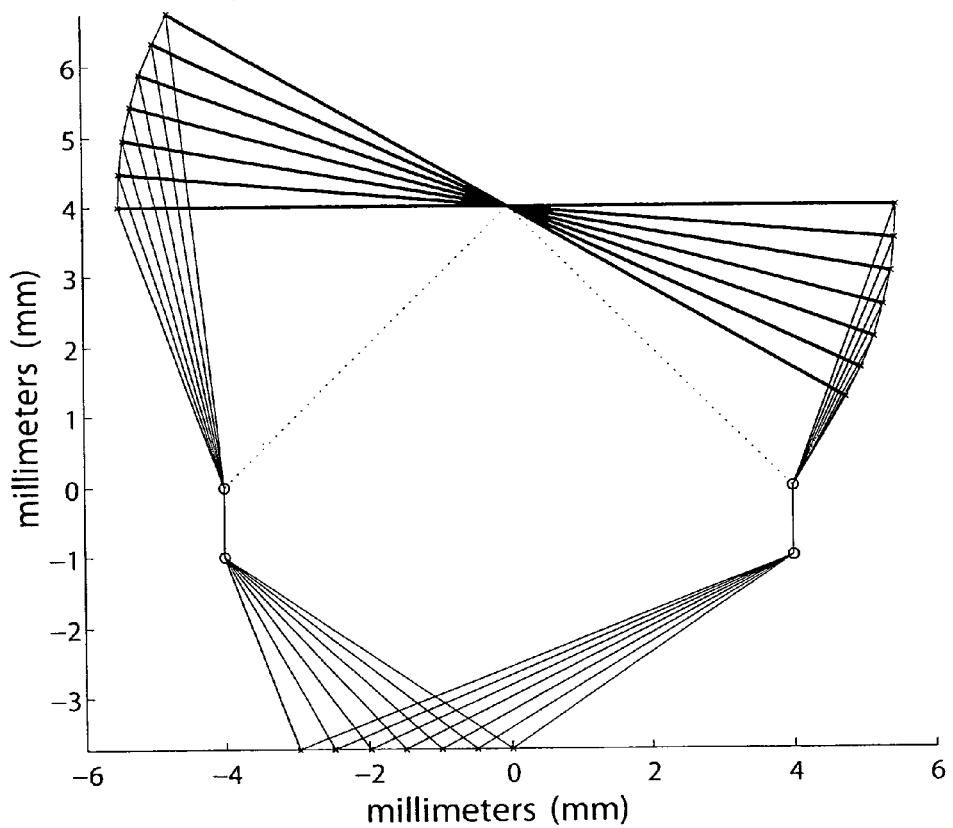
FIGS. 25 to 30D illustrate a specific path length compensation design corresponding to the embodiments of FIGS. 5 to 12.
Figure 26:
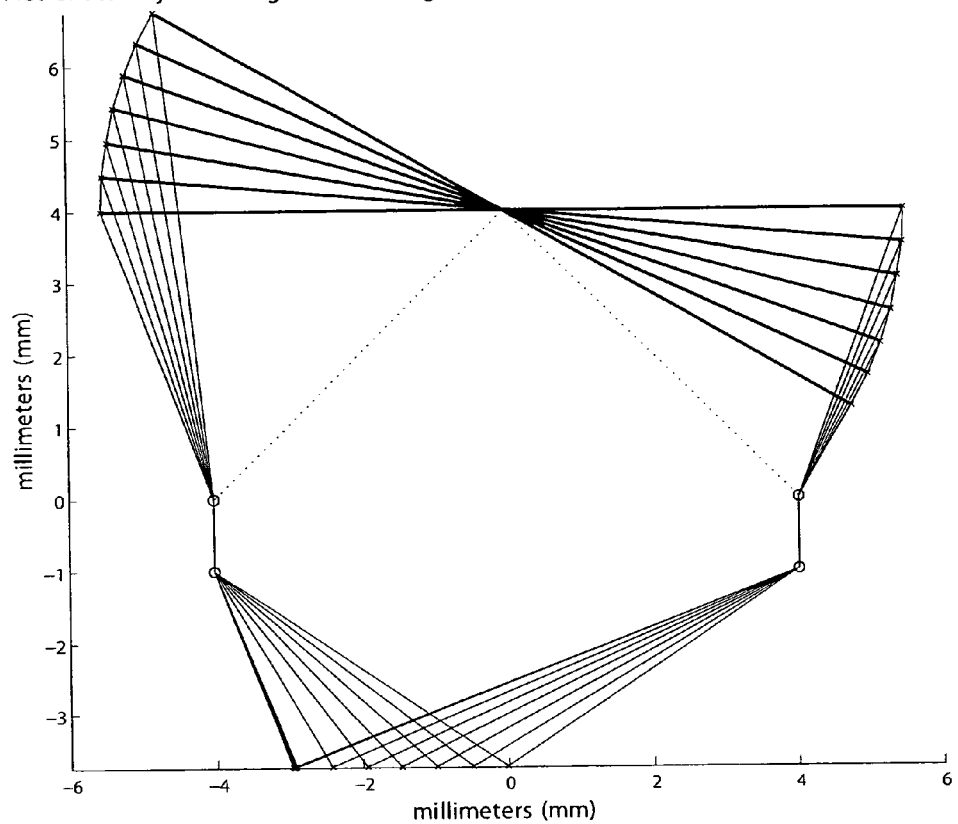
Figure 27:
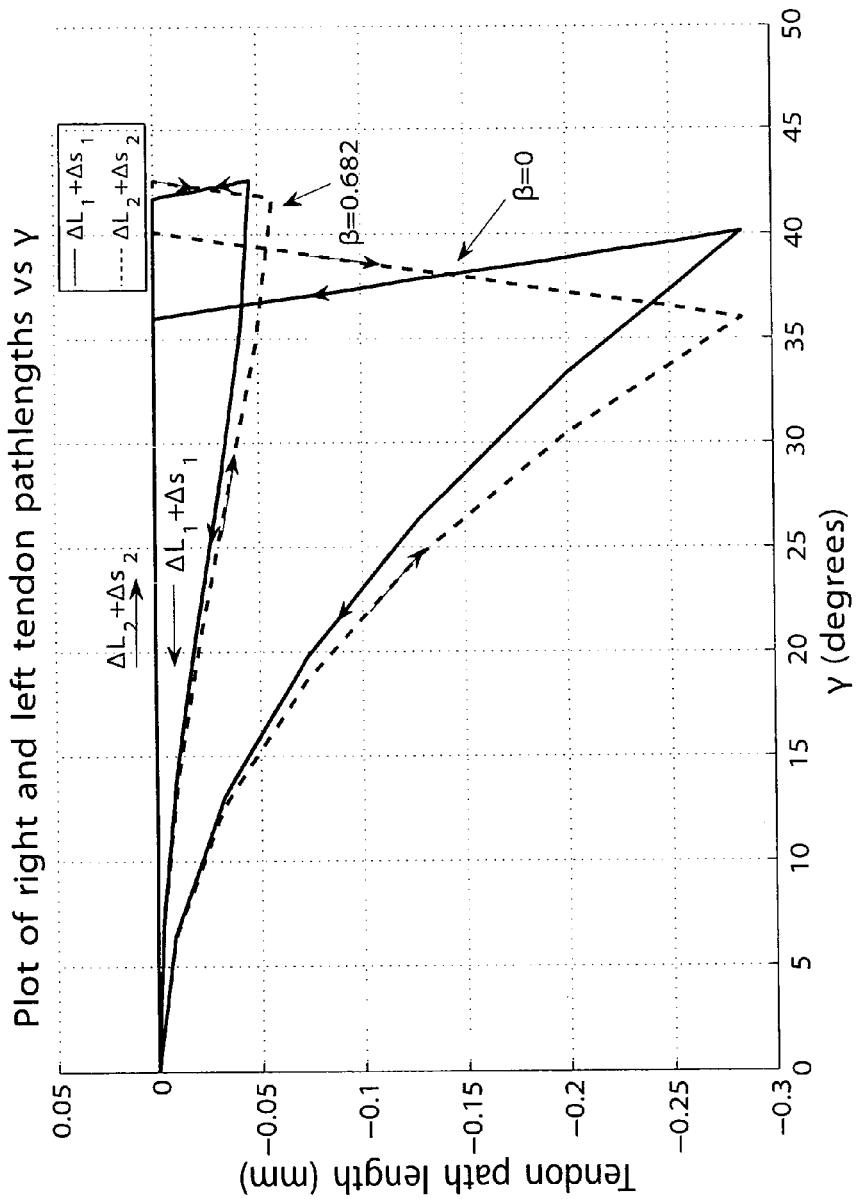
Figure 28:
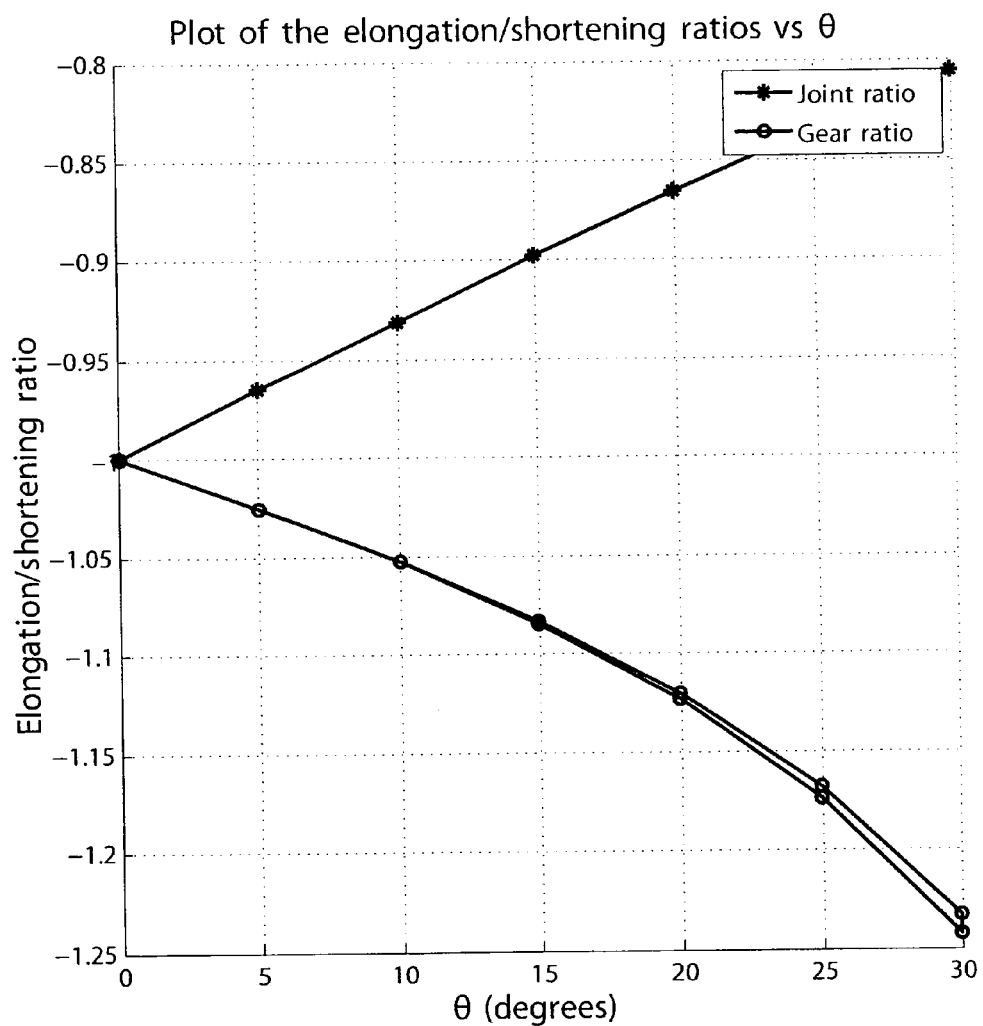
Figure 29:
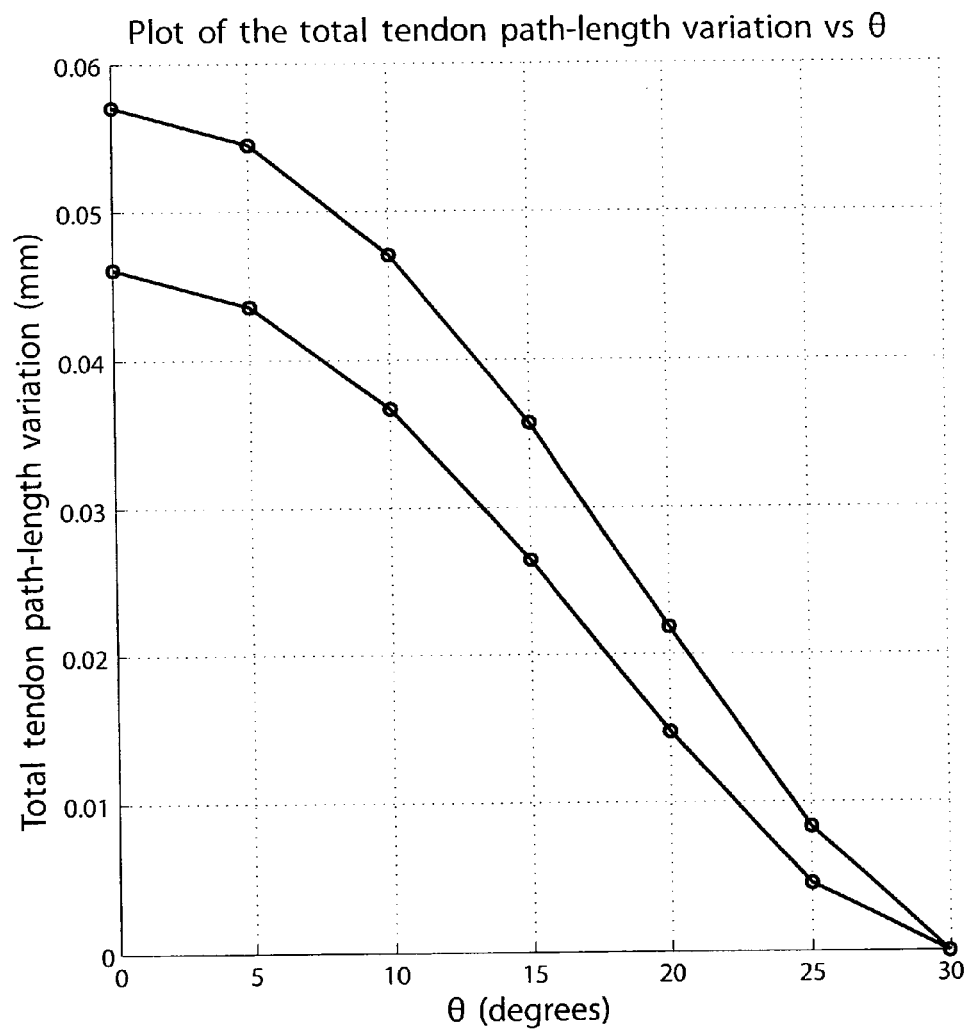
Figure 30A:
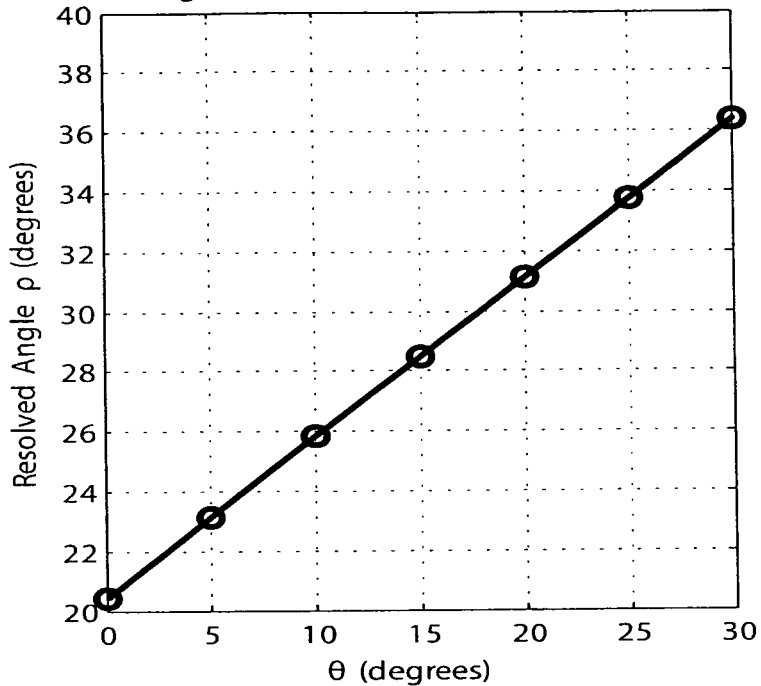
Figure 30B:
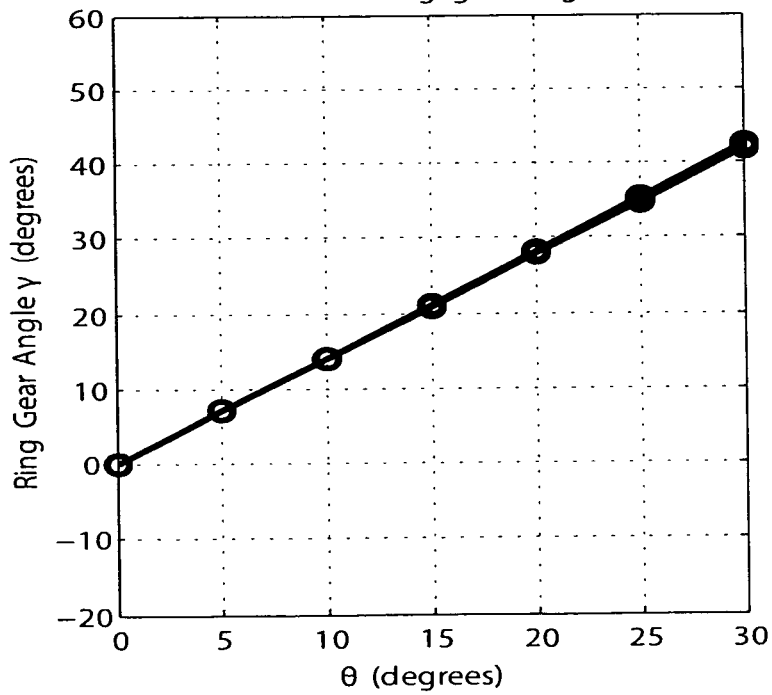
Figure 30C:
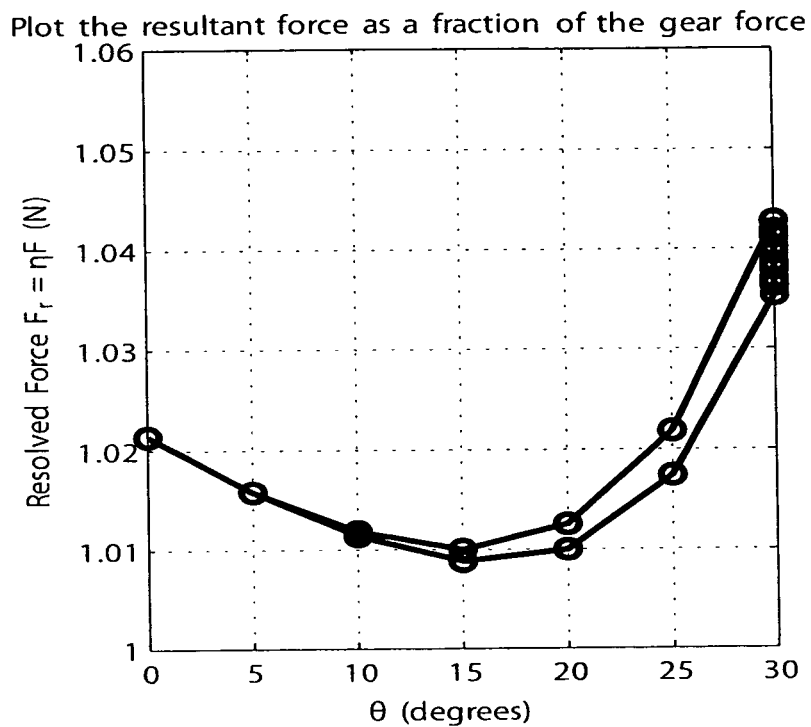
Figure 30D:
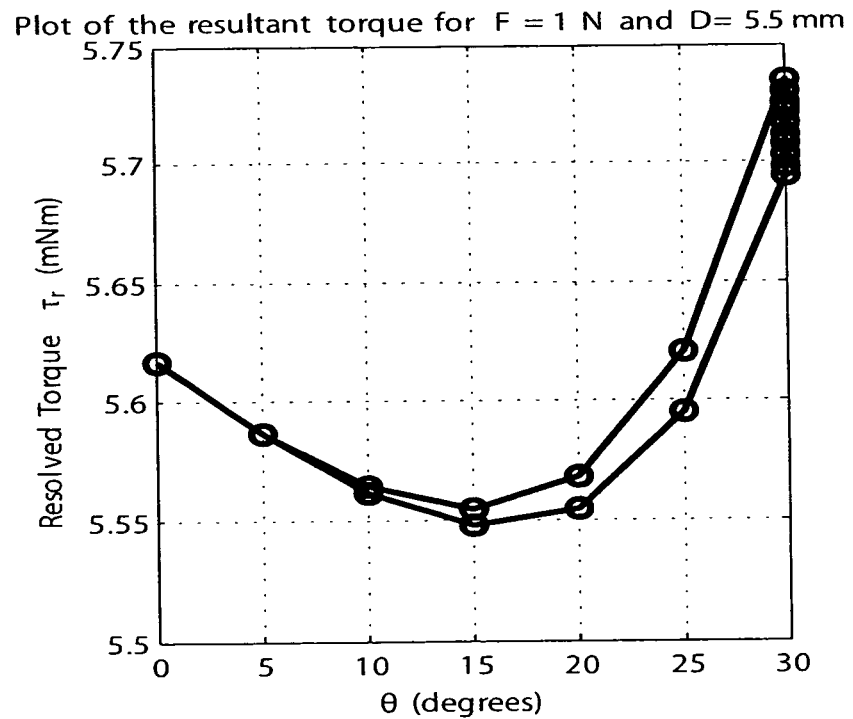
Figure 31:
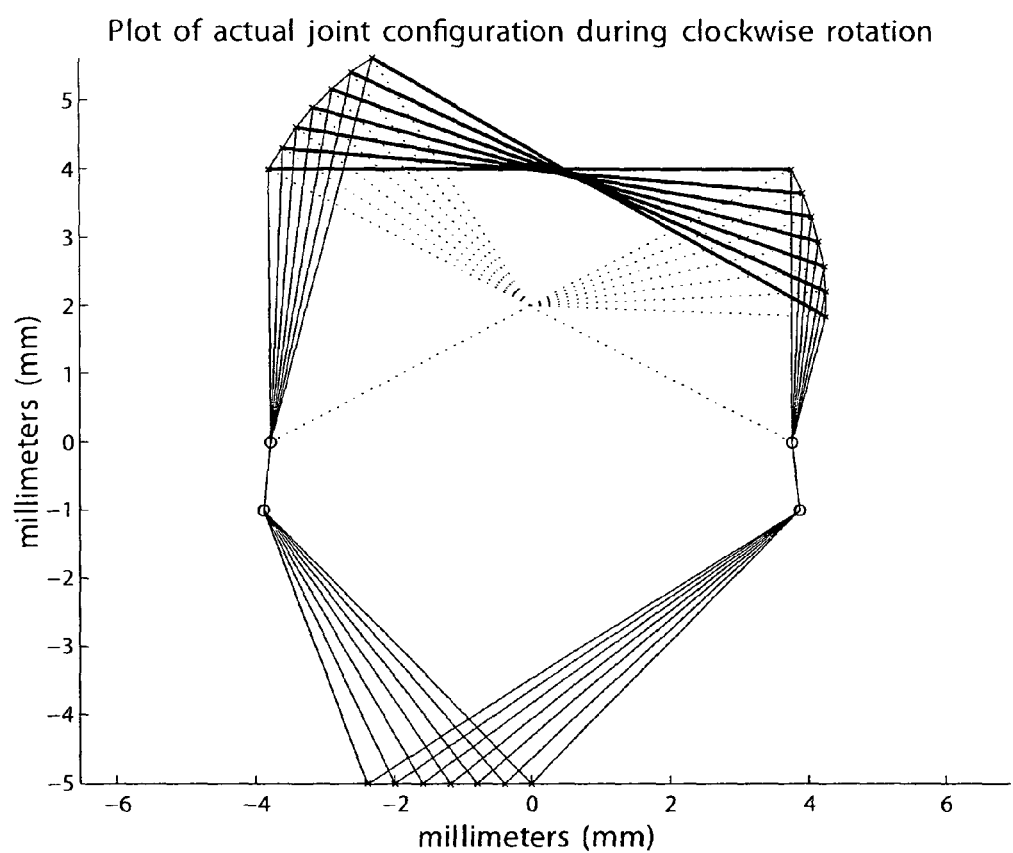
FIGS. 31 to 36D illustrate a specific path length compensation design which is a variation of the design of FIGS. 19 to 24.
Figure 32:
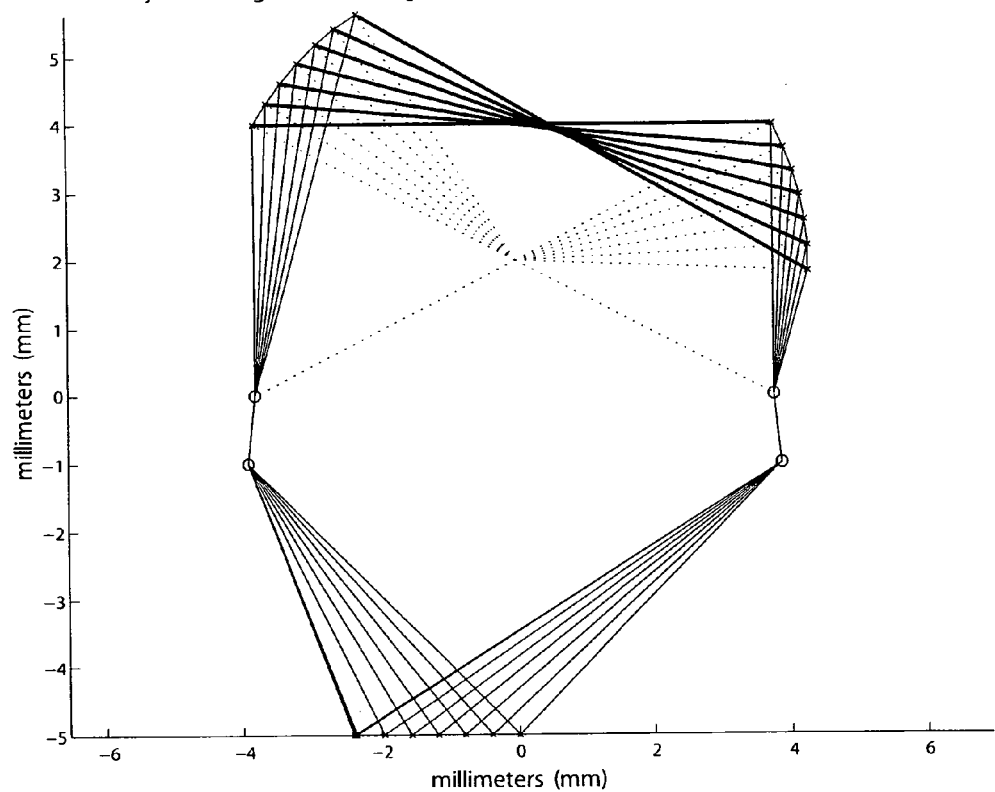
Figure 33:
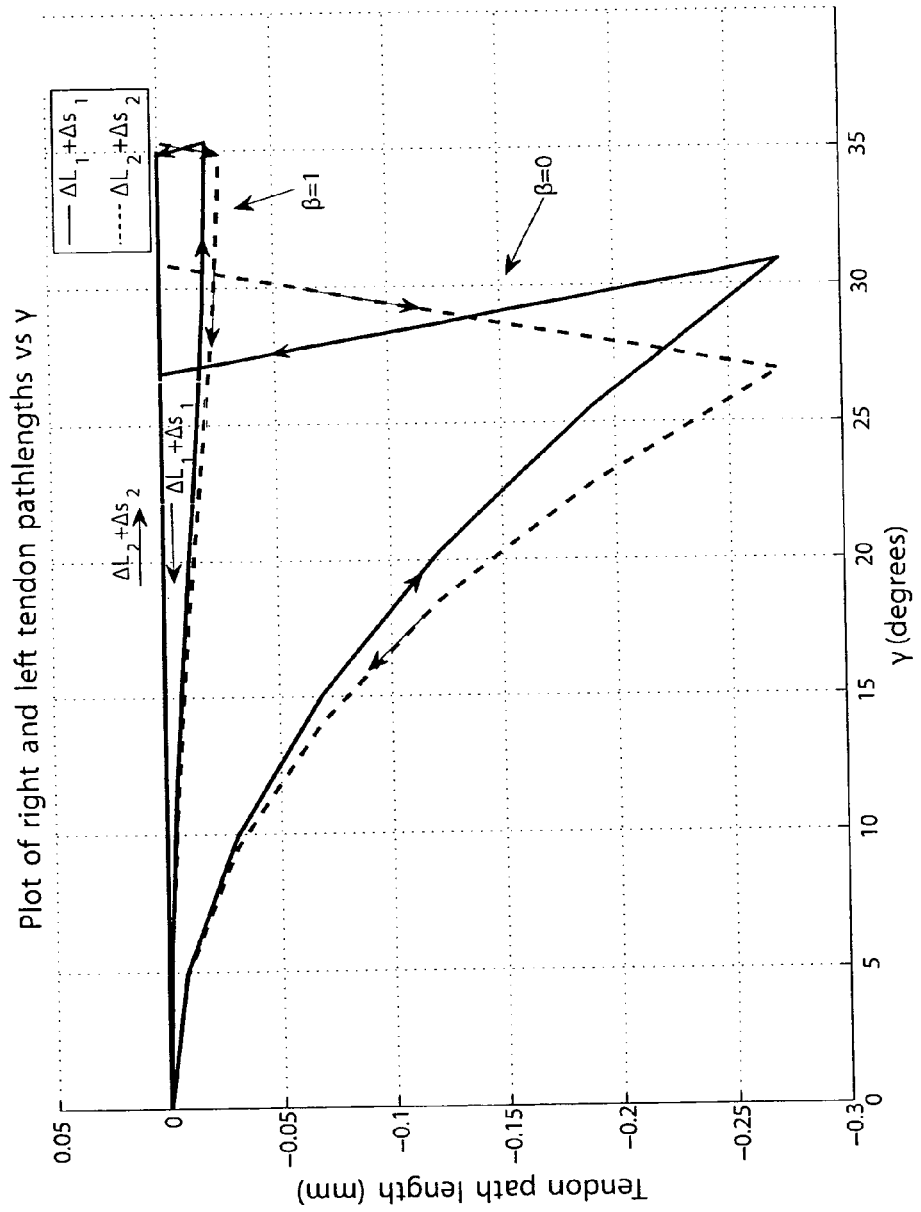
Figure 34:
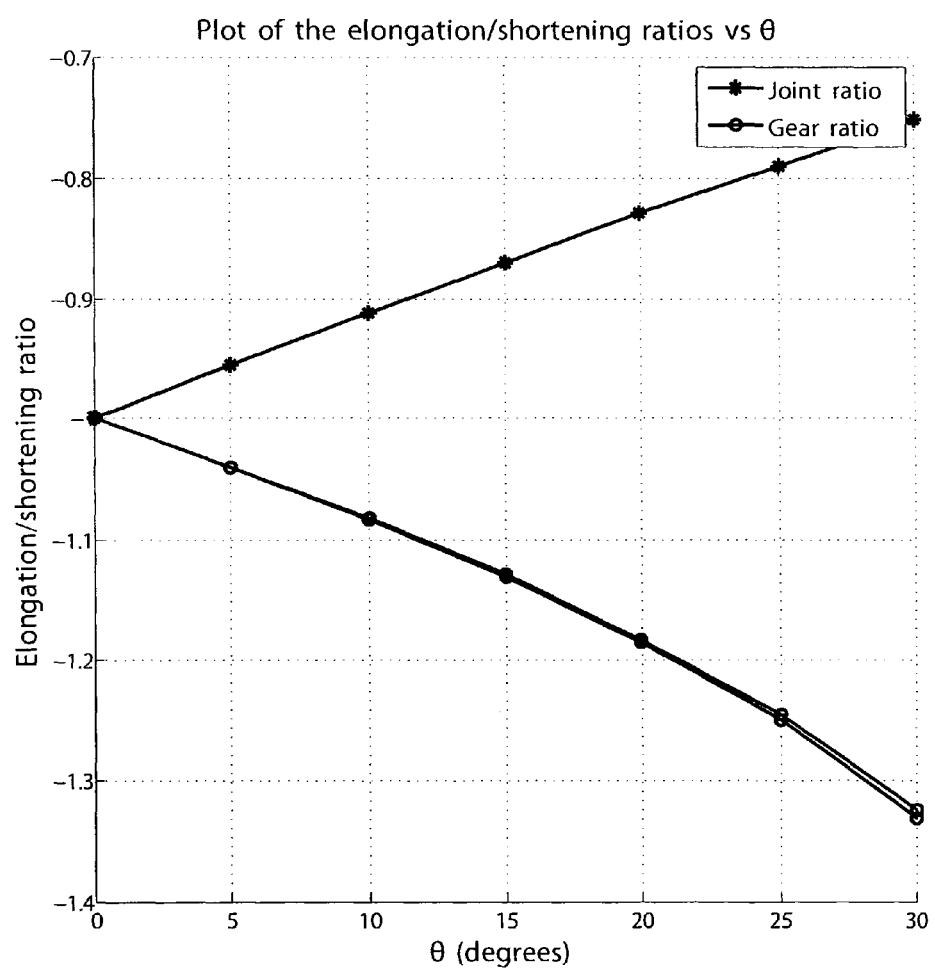
Figure 35:
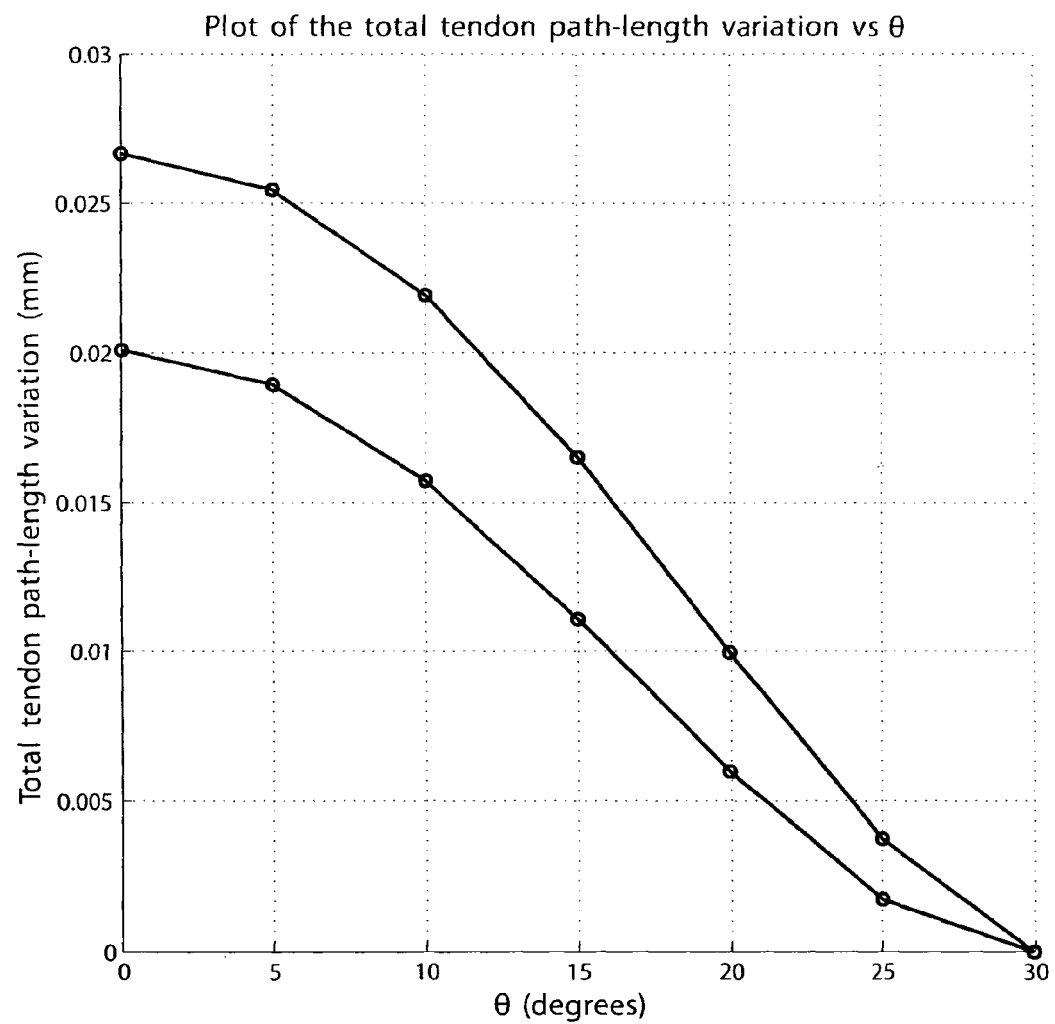
Figure 36A:
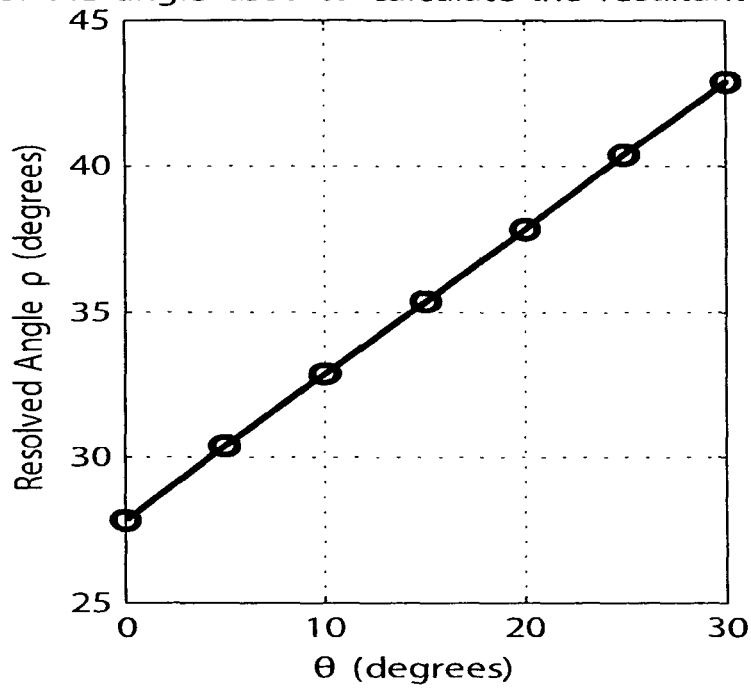
Figure 36B:
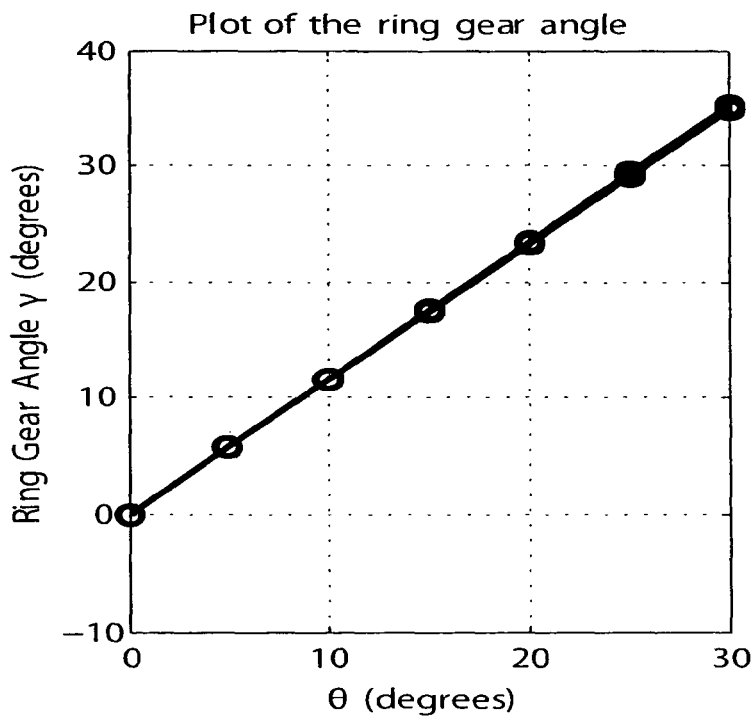
Figure 36C:
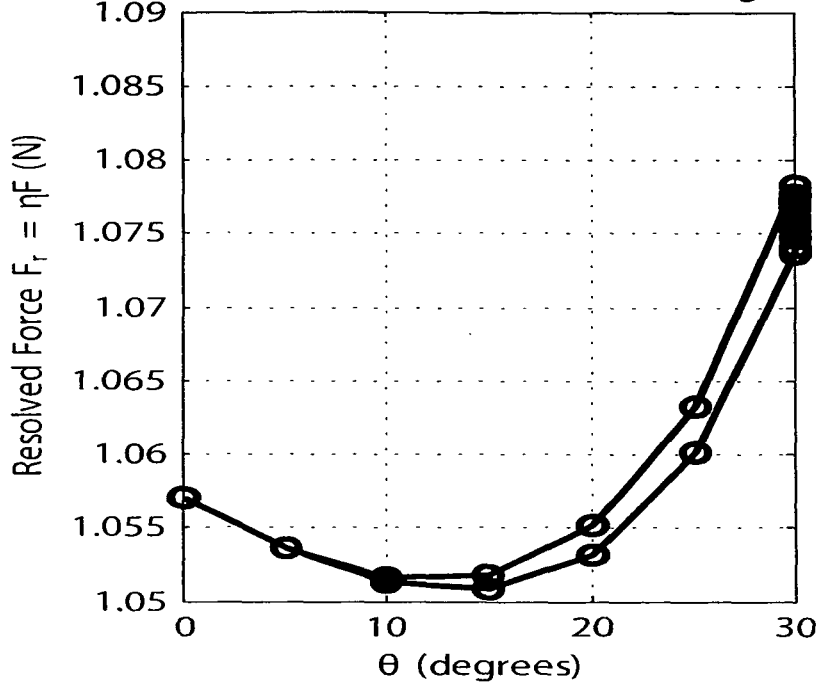
Figure 36D:
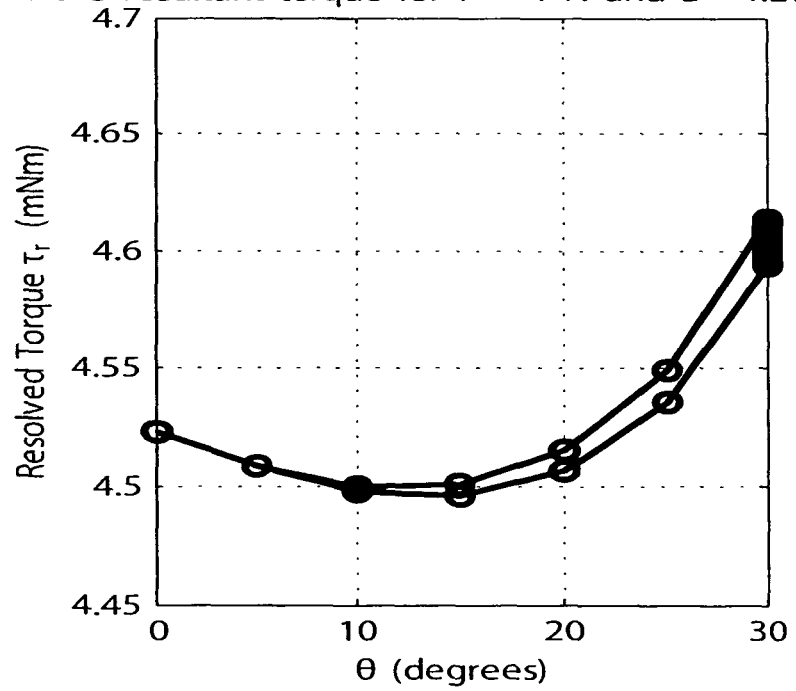
Figure 37:
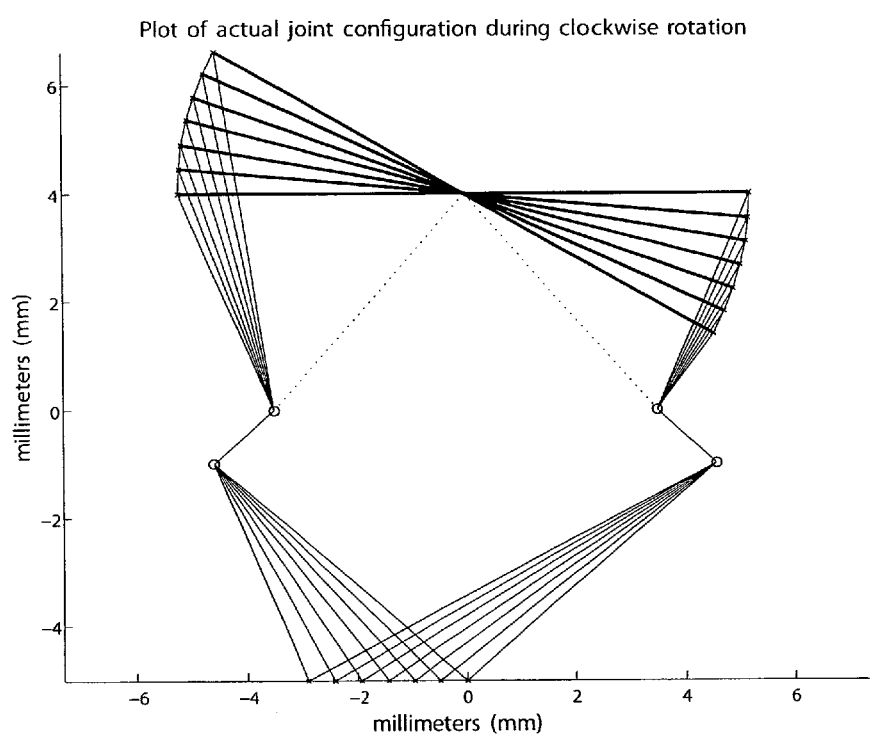
FIGS. 37 to 42D illustrate a specific path length compensation design which is a variation of the design of FIGS. 25 to 30.
Figure 38:
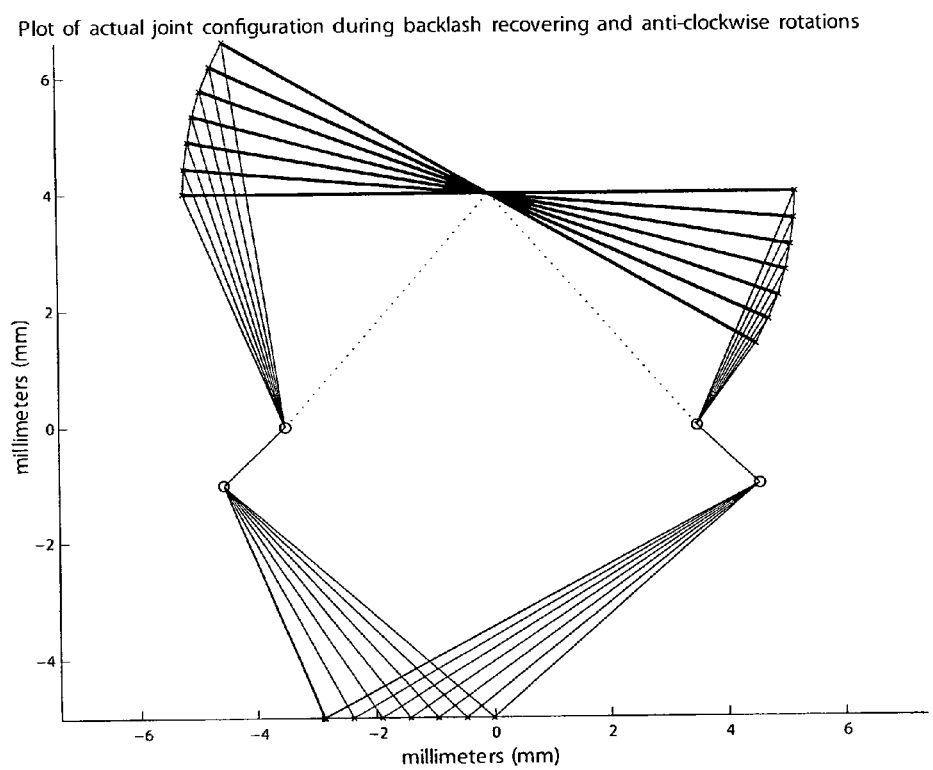
Figure 39:
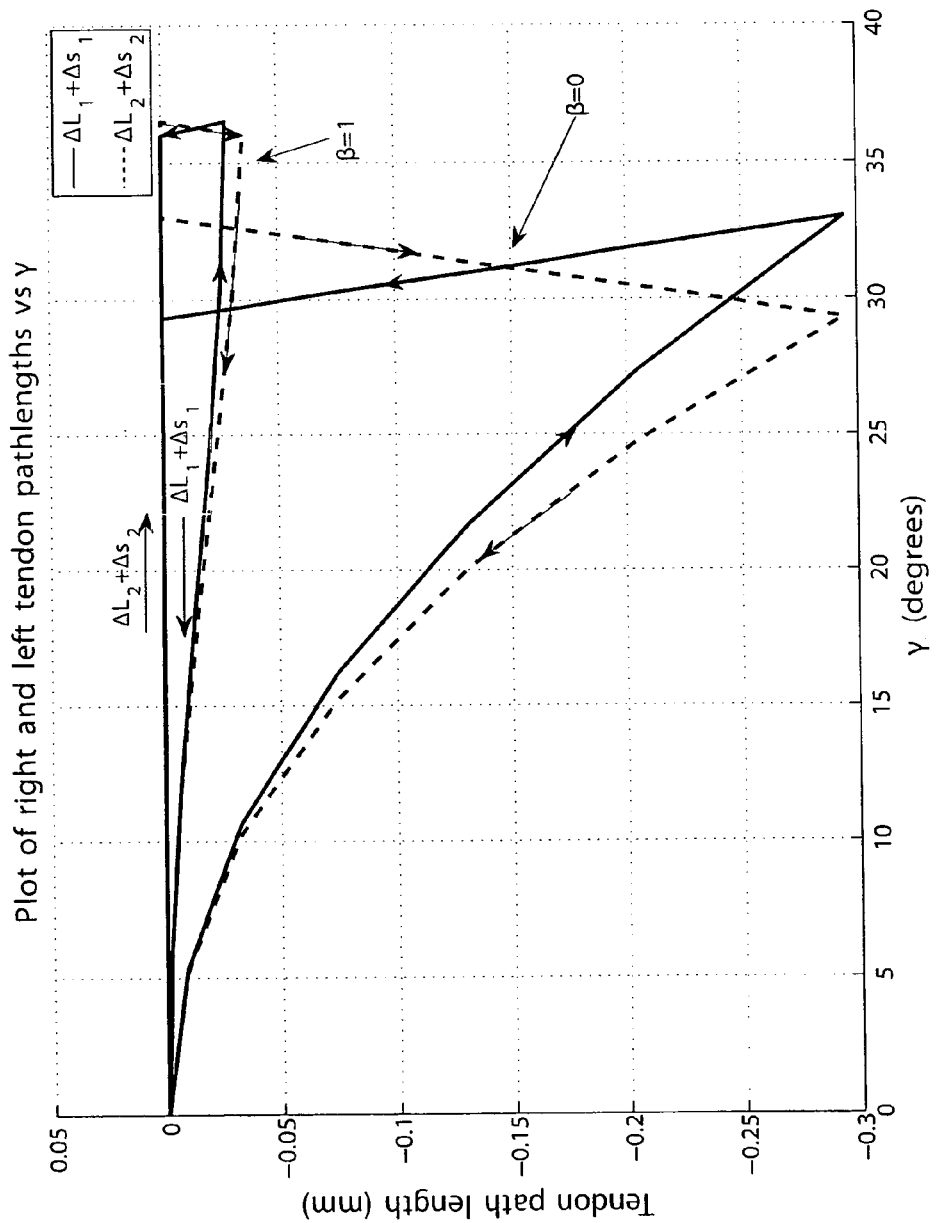
Figure 40:
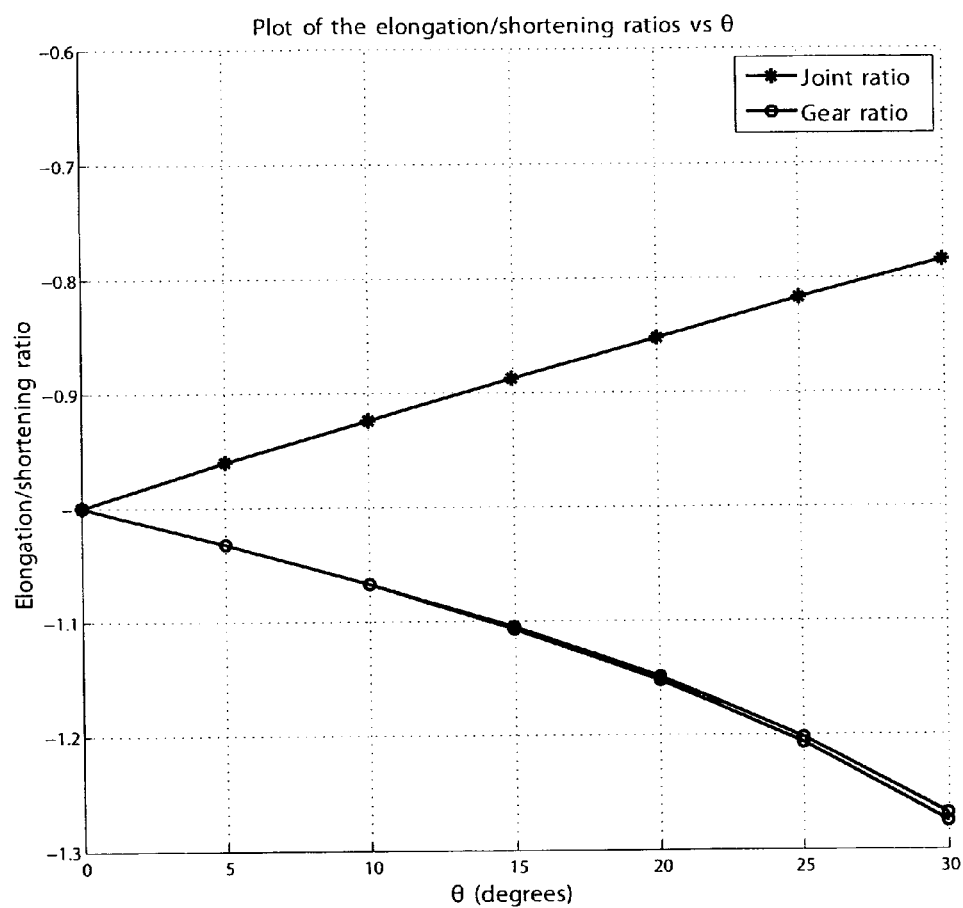
Figure 41:
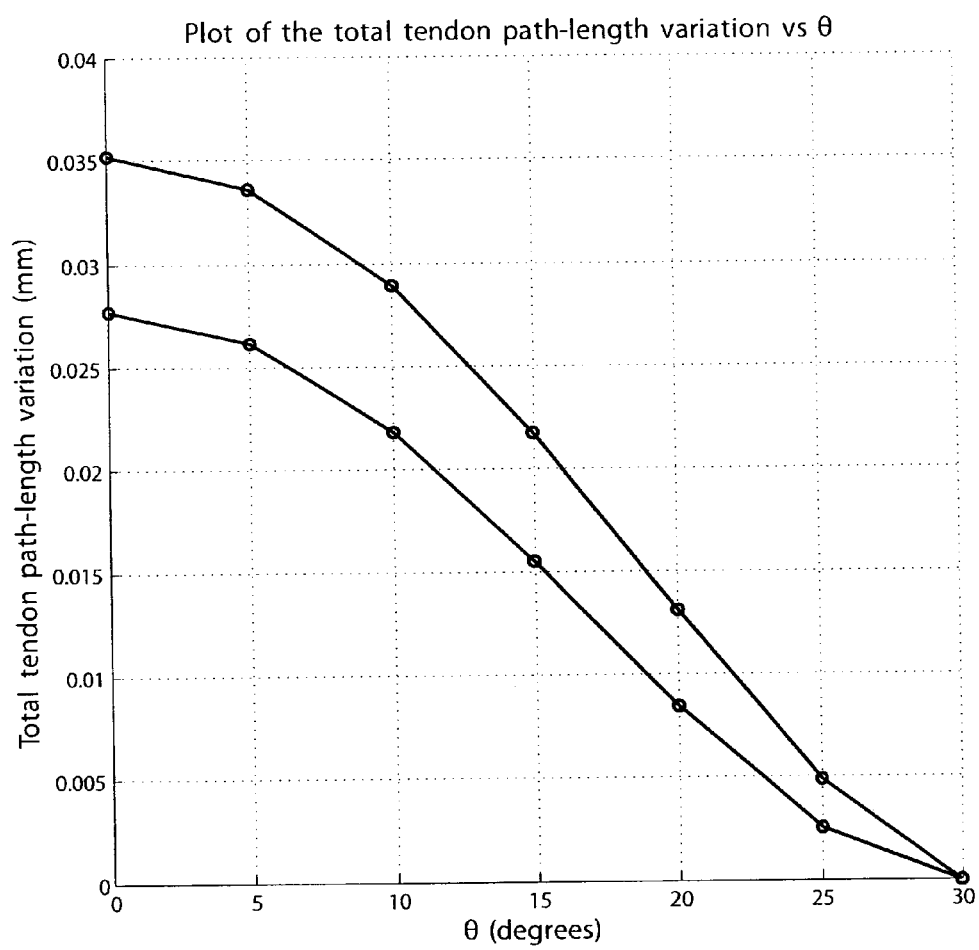
Figure 42A:
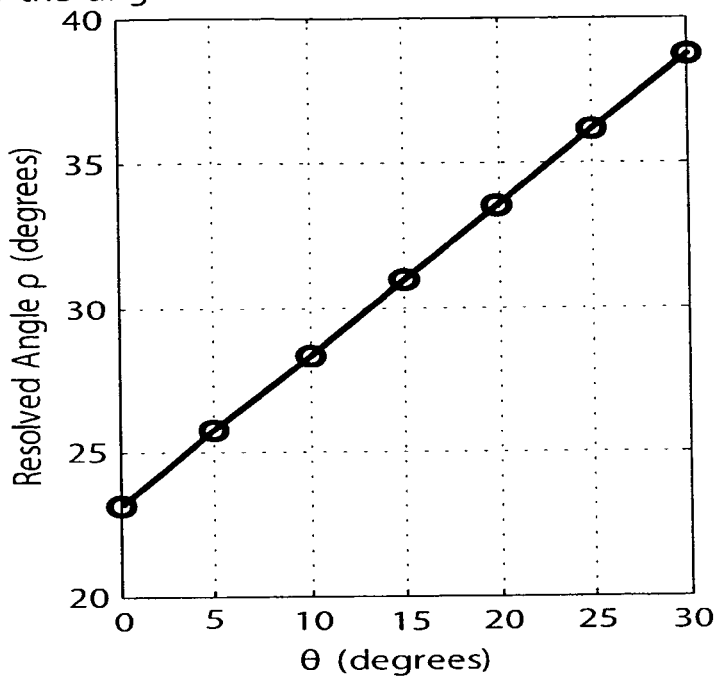
Figure 42B:
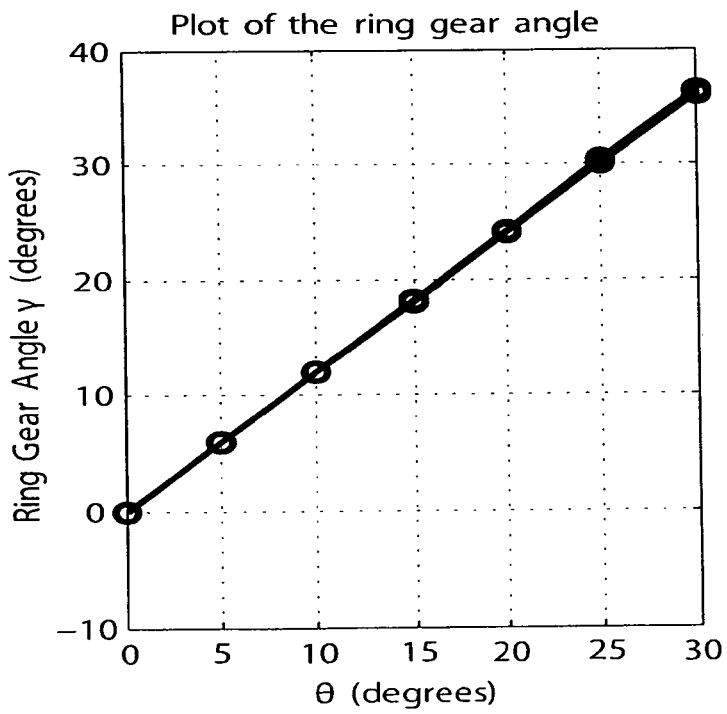
Figure 42C:
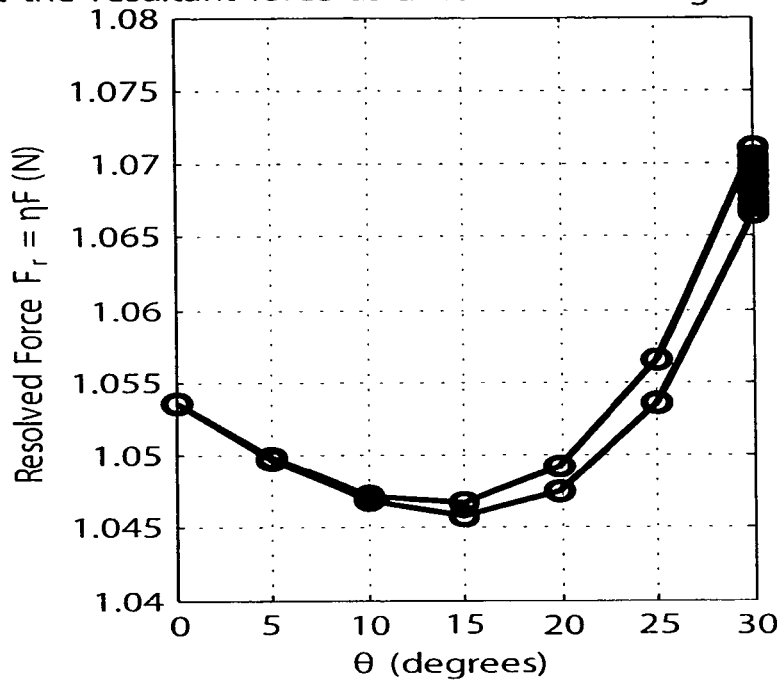
Figure 42D:
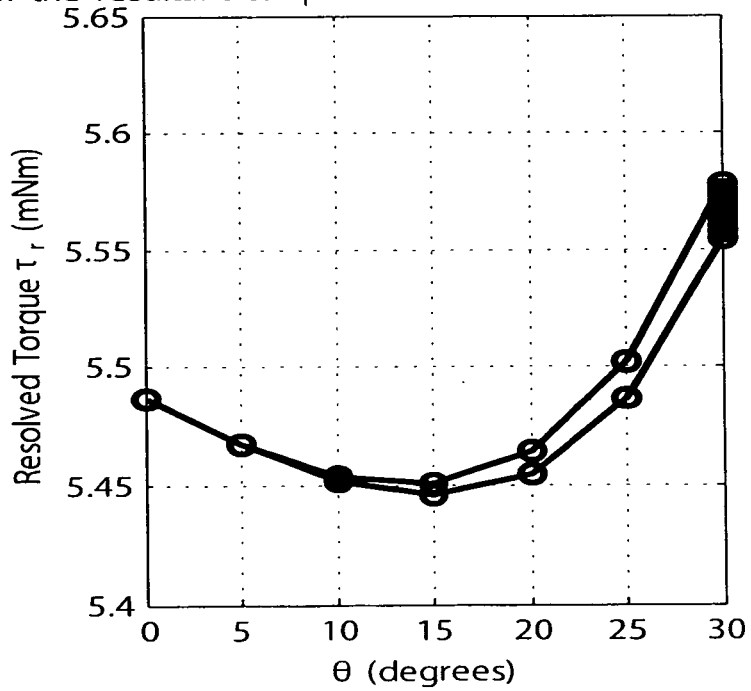

FIG. 22 shows the elongation/shortening ratios with respect to L (labelled as "joint ratio") and s (labelled as "gear ratio"), which are approximately inversely related. FIG. 23 shows the variation in total tendon path length $L_1+L_2+s_1+s_2$ with its minimum value subtracted. The presence of two lines for the gear ratio in FIG. 22 and for the total tendon path length in FIG. 23 is due to the variation of $s_1$ and $s_2$ during the backlash recovering rotation, while $L_1$ and $L_2$ remain constant. This path length changes result in a difference between the gear ratios and total tendon path length variations during clockwise and anti-clockwise rotation.

FIG. 24A-D show plots related to the force transmission in the joint, which illustrate that, for this arrangement, the resulting force $F_r$ and corresponding torque $t_r$ assume the maximum value at the extreme angle of rotation, although the torque reaches the optimisation constraint at one point over the angular range of movement. As discussed above, the difference in force and torque transmission between clockwise and anti-clockwise rotation is due to the backlash recovering period, during which the rotation of the transmission member changes the configuration and path lengths of $s_1$ and $s_2$ while the joint does not rotate, thereby affecting the force transmission.

With reference to FIGS. 25 to 30D introducing an additional constraint of fixing a=0, designs corresponding to the first and second joint members of FIGS. 5 to 11 are obtained. For this case, a=0 and $r_2=r_3$. A design found by an optimisation search is illustrated graphically in FIG. 25 and the design parameters x can readily be derived therefrom.

FIGS. 25 to 30D (corresponding to FIGS. 19 to 24D) show the results for this set of parameters. As is apparent, the backlash angle is somewhat higher, but is still significantly reduced in comparison with the case with β=0. The force transmission efficiency and resulting torque are increased and the torque $t_r$ does not reach the constraint value.

With reference to FIGS. 31 to 36D, the configuration allows a to vary and removes the constraints on $r_2$ and $r_3$. A design found by an optimisation search is illustrated graphically in FIG. 31 and the design parameters x can readily be derived therefrom.

The corresponding results are shown in FIGS. 31 to 36D (corresponding to FIGS. 19 to 24D). As compared with the design described with reference to FIGS. 19 to 24D, the backlash angles are similar and the reduction with respect to the case β=0 is again by a factor of about 10. The force transmission efficiency is also similar.

With reference to FIGS. 37 to 42D, a design is presented with a=0 but allowing $r_2$ and $r_3$ to vary freely. A design found by an optimisation search is illustrated graphically in FIG. 37 and the design parameters x can readily be derived therefrom.

The corresponding results are shown in FIGS. 37 to 42D (corresponding to FIGS. 19 to 24D). As compared to the design described above with reference to FIGS. 25 to 30D, the backlash angle is reduced, while the torque profile shows slightly reduced transmission efficiency.

While, in accordance with the above description, the free parameters of the design (at least β but also one or more of the remaining parameters) may be optimised to get the optimum backlash reduction for a given design, it is important to note that any setting of β>0 would provide some degree of path length compensation and hence backlash reduction. Equally, although the design in FIGS. 16 and 17 provide the lower pulleys (those closest to the attachment point in FIG. 16) between the tendon attachment point and joint plane, path length compensation could also be achieved by placing the lower pulleys on the opposite side of the attachment point so that the attachment point is between the lower pulleys and the joint plane. As long as the plane of movement of the attachment point as the transmission member rotates does not include the line joining the lower pulleys (or, more accurately, the corresponding inflection points of the tendons) some degree of path length compensation may be achieved.

It will be understood that the above description of embodiments of the invention is made for the purpose of illustration and that many alterations, or modifications and/or juxtapositions of the features described above will occur to the skilled person and are intended to be covered by the scope of the appendent claims.

For example, the transmission member 22, although depicted as extending all the way around or within the first joint member 6 may only partially extend around or within the first joint member 6, as long as it remains rotatably secured to it. Likewise, it will be understood that the tendons may comprise a wide variety of filaments, strands, wires, chains, cables etc, any of which may be made of a variety of materials such as metals, for example stainless steel, polymers, for example plastics and nylon, etc. The tendons may be provided as individual tendon portions of any of these materials or as tendon portions of a single length of any of these materials. In the latter case, the length of material is fixedly secured to the transmission member to define the two tendon portions. The transmission member can be driven by means other than meshing gears, for example using a belt or a cable drive arrangement in which the transmission member and the motor are coupled by a belt or cable.

Figure 43:
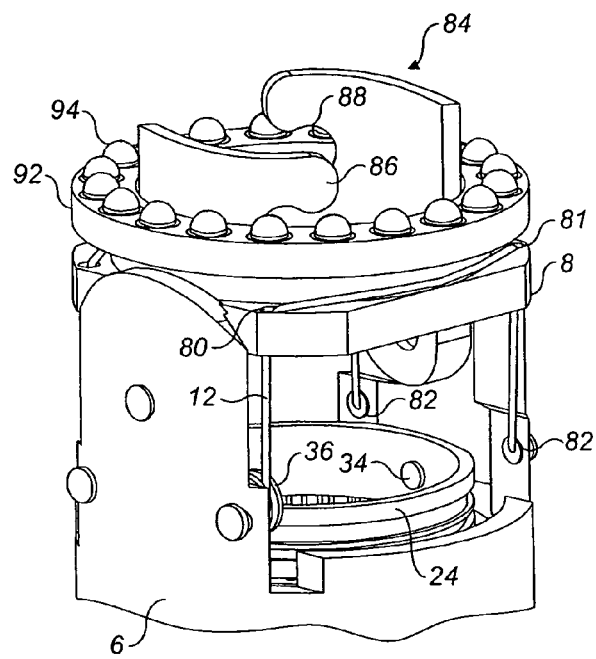
FIG. 43 illustrates a twist lock feature and a further alternative tendon routing arrangement.

With reference to FIG. 43 a twist lock feature for interconnecting joint arrangements or device segments at their respective second joint members and an alternative tendon routing applicable to all embodiments described above is now described.

Regarding the tendon routing, in effect the alternative tendon routing doubles up the tendon to increase the transmittable force by a factor of two. To this end, each tendon portion 12, 14 is attached at one end by a fixation member 34 to the spool 24 (or the length of tendon is attached to the spool 24 in its middle by fixation member 34), from there runs across a pulley 36 and then longitudinally along the joint arrangement to a through hole 80 in the second joint member 8. From there, the tendon is routed across the second joint member 8 along the pivot to a further through hole 81 on the same side of the pivot as the through hole 80 and from there longitudinally back towards the first joint member where the tendon is secured in a fixed relation to the first joint member at an anchor point 82. It will be understood that the tendon does not need to run straight between the through holes 80 and 81 but may follow a curved path to accommodate features of the second joint member 8. Because the pulling force is now shared between the pulley 36 and the attachment point 82, the applicable force is doubled (or from energetic considerations, the same distance travelled by the fixation member 34 now corresponds to half the distance travelled by the through holes 80, 81 giving rise to a corresponding speed reduction and hence force increase).

The second joint member is provided with a twist lock feature 84 which is arranged such that when two second joint members 8 are brought in contact with each other, the respective twist lock features can accommodate each other slidingly and then be lockingly engaged by twisting the respecting joint arrangements relative to each other. To that end, the twist lock feature 84 comprises radially opposed male, hook like feature 86 with a rounded shape adapted to engage a corresponding female features on another joint arrangement. The twist lock feature 84 provides the same female features 88 itself, so that identically shaped twist lock features can engage each other, thereby allowing maximum flexibility in joint arrangements being able to be placed together.

The male feature 86 is shaped to be complimentary to the female feature 88 in a way that a male feature is held securely inside a female feature once the twist lock features have been twisted relative to each other for locking. To this end, the female feature 88 defines an opening for accepting the male feature 86. The opening is narrower than the largest transverse width of the male feature 86, that is the largest width of the male feature 86 taken in a direction perpendicular to a tangential direction in which the male feature moves on twist locking.

To establish electrical interconnection between joint arrangements, a contact member 90 is arranged around the twist lock feature 84 and comprises an annular board 92 supporting a plurality of spring loaded contacts 94 for engaging a corresponding contact on another joint arrangement. The contacts have a rounded free end (and may indeed be partially or fully ball-shaped) which, in addition to the spring loading, facilitates secure contact between respective contacts with a twist lock in place while allowing the contacts to slide past each other during twist locking. Contacts may be established between identical corresponding contacts, that is the contacts on both joint arrangements being joined by the twist lock feature 84 being configured in the same way, or contacts on one of the annular contact boards 94 may be formed simply as fixed contact pads.

It will be appreciated that the tendon routing and twist locks/contact features just described with reference to FIG.

43 are independent of each other and can be applied separately or in combination to any of the embodiments described above or below.

Figure 44:
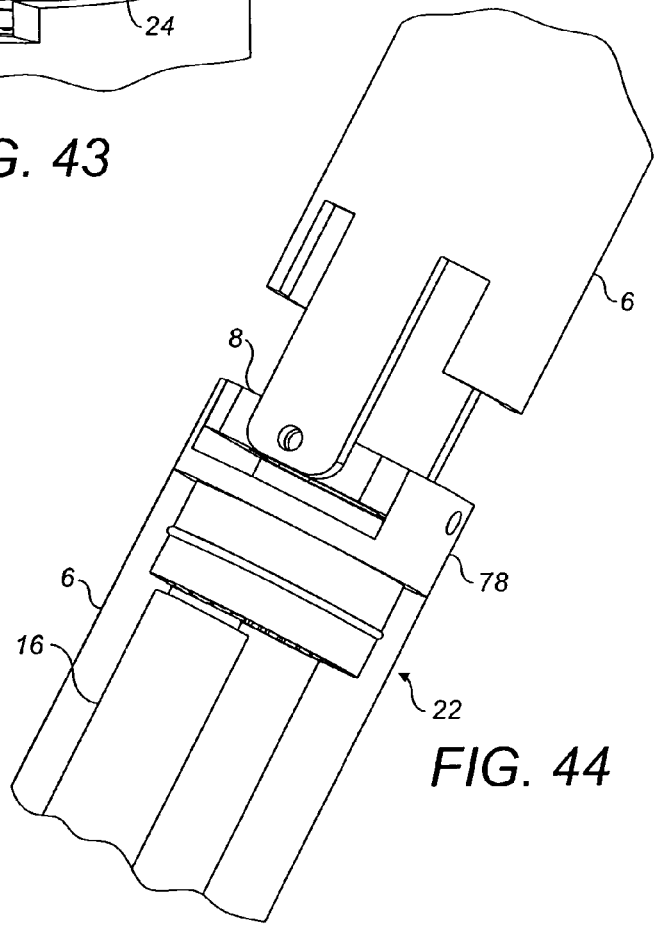
FIG. 44 illustrates a joint arrangement with one longitudinal rotational degree of freedom.

With reference to FIG. 44, the present invention is not limited to joints employing tendons as described above. In some embodiments, the transmission member 22 defines a rotational degree of freedom about a longitudinal axis of the resulting joint arrangement and the same benefits regarding the space saving, yet high speed reduction arrangement of the transmission member applies also to this embodiment. In these embodiments, the transmission member 22 is coupled directly to a connection piece 78 which connects to a further joint member 6 which, in some embodiments, is pivotally connected to the connection piece 78, for example, by a second joint member 8 fixedly coupled to the connection member 78. In some embodiments, the transmission member 22, the connection piece 78 and the second joint member 8 may be formed as unitary piece. Such rotational joints are, in some embodiments, incorporated in the multi-segment devices as described above, and, in some embodiments, include twist lock features and electrical contact arrangements as described above for linking with other segments.

While some embodiments of the invention have been described with reference to endoscopes for medical uses, it will be understood that the invention is not so limited but can be applied to any endoscope and any articulated device, whether hollow or not.

The invention claimed is:

1. A joint arrangement including a first joint member, a transmission member and drive means associated with the first joint member and a second joint member movably linked to the first joint member, wherein the transmission member is disposed at least partially around or against an inner surface of the first joint member and is drivable by the drive means to rotate about an axis lying longitudinally within the first joint member to cause movement of the first and second joint members relative to each other, wherein the first joint member is pivotably linked to the second joint member by a pivot and the joint arrangement comprises first and second tendon portions secured to the second joint member on either side of the pivot, the transmission member being arranged to transmit a force to the first and second tendon portions to cause movement of the second joint member relative to the first joint member, wherein the transmission member defines a spool on which the first and second tendons are wound such that rotation of the spool in one direction pays out the first tendon portion and takes in the second tendon portion and rotation of the spool in the other direction pays out the second tendon portion and takes in the first tendon portion, the joint arrangement includes a tendon routing arrangement defining an inflection point for each tendon portion to route each tendon portion from a direction generally along the spool to a direction generally along the first joint member away from the spool and transmission member, and an attachment point at which the first and second tendon portions are secured to the transmission member travels off a line defined by the inflection points as the transmission member rotates.

2. A joint arrangement as claimed in claim 1, in which the tendon portions are slideably secured to the second joint member and one end of each tendon portion is attached to the first joint member and another end of each tendon portion is attached to the transmission member.

3. A joint arrangement as claimed in claim 1, which defines a through-bore when the first and second joint members are aligned.

4. A joint member as claimed in claim 1 in which the transmission member defines a toothed surface along at least part of its circumference to define a gear and the drive means include a pinion to mesh with the gear.

5. A joint member as claimed in claim 4 in which the tendon portions are secured to the transmission member in contact with a surface adjacent to the toothed surface.

6. A joint arrangement as claimed in claim 1 and a further joint arrangement as claimed in claim 1, the joint arrangement and further joint arrangement being mounted together at respective second joint members or comprising a common second joint member such that a pivot axis of the joint arrangement is perpendicular to a pivot axis of the further joint arrangement to define a two degree of freedom joint.

7. A joint arrangement as claimed in claim 1 in which the drive means is disposed within the first joint member.

8. A joint arrangement as claimed in claim 1 wherein the transmission member is disposed within the first member against an inner surface of the first joint member.

9. A joint arrangement as claimed in claim 1, the second joint member defining a twist lock feature for securing the second joint member to another joint arrangement.

10. A joint arrangement as claimed in claim 9, the second joint member including electrical contacts for sliding engaging corresponding contacts on the other joint arrangement as the twist lock feature is locked.

11. A segmented device comprising a plurality of joint arrangements as claimed in claim 1.

12. A segmented device as claimed in claim 11 in which the joints are disposed relative to each other to define an instrument bore through the joints for passing an instrument through the device.

13. An endoscope comprising a segmented device as claimed in claim 11.

14. A surgical tool for minimally invasive surgery comprising a segmented device as claimed in claim 11.

* * * * *